United States Patent
Hsieh et al.

(10) Patent No.: US 10,398,786 B2
(45) Date of Patent: Sep. 3, 2019

(54) THERAPEUTIC GENE COCKTAIL FOR HEART REGENERATION

(71) Applicant: Academia Sinica, Taipei (TW)

(72) Inventors: Patrick C. H. Hsieh, Taipei (TW); Yuan-Yuan Cheng, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/567,931

(22) PCT Filed: Apr. 19, 2016

(86) PCT No.: PCT/US2016/028249
§ 371 (c)(1),
(2) Date: Oct. 19, 2017

(87) PCT Pub. No.: WO2016/172082
PCT Pub. Date: Oct. 27, 2016

(65) Prior Publication Data
US 2018/0099056 A1    Apr. 12, 2018

Related U.S. Application Data

(60) Provisional application No. 62/149,854, filed on Apr. 20, 2015.

(51) Int. Cl.
| | | |
|---|---|---|
| *A61P 9/10* | (2006.01) | |
| *A61K 38/17* | (2006.01) | |
| *A61K 45/06* | (2006.01) | |
| *A61K 48/00* | (2006.01) | |
| *A61K 31/713* | (2006.01) | |

(52) U.S. Cl.
CPC .......... *A61K 48/005* (2013.01); *A61K 31/713* (2013.01); *A61K 38/1709* (2013.01); *A61K 45/06* (2013.01); *A61P 9/10* (2018.01); *C12N 2310/531* (2013.01); *C12N 2710/10343* (2013.01)

(58) Field of Classification Search
CPC ......... A61K 48/005; A61K 45/06; A61P 9/10; A01K 2207/05; C12N 15/1113
See application file for complete search history.

(56) References Cited

U.S. PATENT DOCUMENTS

| | | | | |
|---|---|---|---|---|
| 2007/0059685 A1* | 3/2007 | Kohne | ................ | C12Q 1/6809 435/5 |
| 2011/0110916 A1 | 5/2011 | Worman et al. | | |
| 2015/0301055 A1* | 10/2015 | Spetzler | ............... | G01N 33/574 506/9 |
| 2017/0266253 A1* | 9/2017 | Chang | ................... | A61K 38/12 |

FOREIGN PATENT DOCUMENTS

WO    WO 2014/065435 A1    5/2014

OTHER PUBLICATIONS

Bolte et al., Expression of Foxml transcription factor in cardiomyocytes is required for myocardial development. PLoS One. 2011;6(7):e22217. doi: 10.1371/journal.pone.0022217. Epub Jul. 14, 2011.
Engel et al., p38 MAP kinase inhibition enables proliferation of adult mammalian cardiomyocytes. Genes Dev. May 15, 2005;19(10):1175-87. Epub May 3, 2005.
Naqvi et al., A proliferative burst during preadolescence establishes the final cardiomyocyte number. Cell. May 8, 2014;157(4):795-807. doi: 10.1016/j.cell.2014.03.035.
Ramakrishna et al., Myocardium defects and ventricular hypoplasia in mice homozygous null for the Forkhead Box M1 transcription factor. Dev Dyn. Apr. 2007;236(4):1000-13.
Takahashi et al., Induction of pluripotent stem cells from mouse embryonic and adult fibroblast cultures by defined factors. Cell. Aug. 25, 2006; 126(4):663-76. Epub Aug. 10, 2006.
Xu et al., Highly efficient derivation of ventricular cardiomyocytes from induced pluripotent stem cells with a distinct epigenetic signature. Cell Res. Jan. 2012;22(1):142-54. doi: 10.1038/cr.2011. 171. Epub Nov. 8, 2011.
Yang et al., Id proteins in the vasculature: from molecular biology to cardiopulmonary medicine. Cardiovasc Res. Dec. 1, 2014;104(3):388-98. doi: 10.1093/cvr/cvu215. Epub Oct. 1, 2014.

* cited by examiner

*Primary Examiner* — Brian Whiteman
(74) *Attorney, Agent, or Firm* — Wolf, Greenfield & Sacks, P.C.

(57) ABSTRACT

A combination of active agents selected from a FoxM1 enhancer, an Id1 enhancer, and a JNK3 inhibitor and the uses thereof in promoting cardiomyocyte proliferation and treating heart diseases in a subject in need of the treatment.

30 Claims, 11 Drawing Sheets

Specification includes a Sequence Listing.

SEQUENCE LISTING

<160> NUMBER OF SEQ ID NOS: 7

<210> SEQ ID NO 1
<211> LENGTH: 21

```
<212> TYPE: DNA
<213> ORGANISM: Artificial Sequence
<220> FEATURE:
<223> OTHER INFORMATION: Synthetic Polynucleotide

<400> SEQUENCE: 1
caatagagag atccaacata a                                              21

<210> SEQ ID NO 2
<211> LENGTH: 801
<212> TYPE: PRT
<213> ORGANISM: Homo sapiens

<400> SEQUENCE: 2
```

| Met | Lys | Thr | Ser | Pro | Arg | Arg | Pro | Leu | Ile | Leu | Lys | Arg | Arg | Leu |
|---|---|---|---|---|---|---|---|---|---|---|---|---|---|---|
| 1 | | | | 5 | | | | | 10 | | | | | 15 |

| Pro | Leu | Pro | Val | Gln | Asn | Ala | Pro | Ser | Glu | Thr | Ser | Glu | Glu | Pro |
|---|---|---|---|---|---|---|---|---|---|---|---|---|---|---|
| | | | 20 | | | | | 25 | | | | | 30 | |

| Lys | Arg | Ser | Pro | Ala | Gln | Gln | Glu | Ser | Asn | Gln | Ala | Glu | Ala | Ser | Lys |
|---|---|---|---|---|---|---|---|---|---|---|---|---|---|---|---|
| | | 35 | | | | | 40 | | | | | 45 | | | |

| Glu | Val | Ala | Glu | Ser | Asn | Ser | Cys | Lys | Phe | Pro | Ala | Gly | Ile | Lys | Ile |
|---|---|---|---|---|---|---|---|---|---|---|---|---|---|---|---|
| 50 | | | | | 55 | | | | | 60 | | | | | |

| Ile | Asn | His | Pro | Thr | Met | Pro | Asn | Thr | Gln | Val | Val | Ala | Ile | Pro | Asn |
|---|---|---|---|---|---|---|---|---|---|---|---|---|---|---|---|
| 65 | | | | | 70 | | | | | 75 | | | | | 80 |

| Asn | Ala | Asn | Ile | His | Ser | Ile | Ile | Thr | Ala | Leu | Thr | Ala | Lys | Gly | Lys |
|---|---|---|---|---|---|---|---|---|---|---|---|---|---|---|---|
| | | | | 85 | | | | | 90 | | | | | 95 | |

| Glu | Ser | Gly | Ser | Ser | Gly | Pro | Asn | Lys | Phe | Ile | Leu | Ile | Ser | Cys | Gly |
|---|---|---|---|---|---|---|---|---|---|---|---|---|---|---|---|
| | | | 100 | | | | | 105 | | | | | 110 | | |

| Gly | Ala | Pro | Thr | Gln | Pro | Pro | Gly | Leu | Arg | Pro | Gln | Thr | Gln | Thr | Ser |
|---|---|---|---|---|---|---|---|---|---|---|---|---|---|---|---|
| | | 115 | | | | | 120 | | | | | 125 | | | |

| Tyr | Asp | Ala | Lys | Arg | Thr | Glu | Val | Thr | Leu | Glu | Thr | Leu | Gly | Pro | Lys |
|---|---|---|---|---|---|---|---|---|---|---|---|---|---|---|---|
| | 130 | | | | | 135 | | | | | 140 | | | | |

| Pro | Ala | Ala | Arg | Asp | Val | Asn | Leu | Pro | Arg | Pro | Pro | Gly | Ala | Leu | Cys |
|---|---|---|---|---|---|---|---|---|---|---|---|---|---|---|---|
| 145 | | | | | 150 | | | | | 155 | | | | | 160 |

| Glu | Gln | Lys | Arg | Glu | Thr | Cys | Ala | Asp | Gly | Glu | Ala | Ala | Gly | Cys | Thr |
|---|---|---|---|---|---|---|---|---|---|---|---|---|---|---|---|
| | | | | 165 | | | | | 170 | | | | | 175 | |

| Ile | Asn | Asn | Ser | Leu | Ser | Asn | Ile | Gln | Trp | Leu | Arg | Lys | Met | Ser | Ser |
|---|---|---|---|---|---|---|---|---|---|---|---|---|---|---|---|
| | | | 180 | | | | | 185 | | | | | 190 | | |

| Asp | Gly | Leu | Gly | Ser | Arg | Ser | Ile | Lys | Gln | Glu | Met | Glu | Glu | Lys | Glu |
|---|---|---|---|---|---|---|---|---|---|---|---|---|---|---|---|
| | | 195 | | | | | 200 | | | | | 205 | | | |

| Asn | Cys | His | Leu | Glu | Gln | Arg | Gln | Val | Lys | Val | Glu | Glu | Pro | Ser | Arg |
|---|---|---|---|---|---|---|---|---|---|---|---|---|---|---|---|
| | 210 | | | | | 215 | | | | | 220 | | | | |

| Pro | Ser | Ala | Ser | Trp | Gln | Asn | Ser | Val | Ser | Glu | Arg | Pro | Pro | Tyr | Ser |
|---|---|---|---|---|---|---|---|---|---|---|---|---|---|---|---|
| 225 | | | | | 230 | | | | | 235 | | | | | 240 |

| Tyr | Met | Ala | Met | Ile | Gln | Phe | Ala | Ile | Asn | Ser | Thr | Glu | Arg | Lys | Arg |
|---|---|---|---|---|---|---|---|---|---|---|---|---|---|---|---|
| | | | | 245 | | | | | 250 | | | | | 255 | |

| Met | Thr | Leu | Lys | Asp | Ile | Tyr | Thr | Trp | Ile | Glu | Asp | His | Phe | Pro | Tyr |
|---|---|---|---|---|---|---|---|---|---|---|---|---|---|---|---|
| | | | 260 | | | | | 265 | | | | | 270 | | |

| Phe | Lys | His | Ile | Ala | Lys | Pro | Gly | Trp | Lys | Asn | Ser | Ile | Arg | His | Asn |
|---|---|---|---|---|---|---|---|---|---|---|---|---|---|---|---|
| | | 275 | | | | | 280 | | | | | 285 | | | |

| Leu | Ser | Leu | His | Asp | Met | Phe | Val | Arg | Glu | Thr | Ser | Ala | Asn | Gly | Lys |
|---|---|---|---|---|---|---|---|---|---|---|---|---|---|---|---|
| | 290 | | | | | 295 | | | | | 300 | | | | |

| Val | Ser | Phe | Trp | Thr | Ile | His | Pro | Ser | Ala | Asn | Arg | Tyr | Leu | Thr | Leu |
|---|---|---|---|---|---|---|---|---|---|---|---|---|---|---|---|
| 305 | | | | | 310 | | | | | 315 | | | | | 320 |

| Asp | Gln | Val | Phe | Lys | Pro | Leu | Asp | Pro | Gly | Ser | Pro | Gln | Leu | Pro | Glu |
|---|---|---|---|---|---|---|---|---|---|---|---|---|---|---|---|
| | | | | 325 | | | | | 330 | | | | | 335 | |

```
His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
            355                 360                 365

Pro Leu Leu Pro Arg Val Ser Ser Tyr Leu Val Pro Ile Gln Phe Pro
370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
            435                 440                 445

Thr Ser Leu Phe Asn Phe Ile Phe Leu Cys Leu Ser Val Leu Leu Ala
            450                 455                 460

Glu Glu Gly Ile Ala Pro Leu Ser Ser Ala Gly Pro Gly Lys Glu Glu
465                 470                 475                 480

Lys Leu Leu Phe Gly Glu Gly Phe Ser Pro Leu Leu Pro Val Gln Thr
                485                 490                 495

Ile Lys Glu Glu Glu Ile Gln Pro Gly Glu Glu Met Pro His Leu Ala
            500                 505                 510

Arg Pro Ile Lys Val Glu Ser Pro Pro Leu Glu Glu Trp Pro Ser Pro
            515                 520                 525

Ala Pro Ser Phe Lys Glu Ser Ser His Ser Trp Glu Asp Ser Ser
            530                 535                 540

Gln Ser Pro Thr Pro Arg Pro Lys Lys Ser Tyr Ser Gly Leu Arg Ser
545                 550                 555                 560

Pro Thr Arg Cys Val Ser Glu Met Leu Val Ile Gln His Arg Glu Arg
                565                 570                 575

Arg Glu Arg Ser Arg Ser Arg Arg Lys Gln His Leu Leu Pro Pro Cys
            580                 585                 590

Val Asp Glu Pro Glu Leu Leu Phe Ser Glu Gly Pro Ser Thr Ser Arg
            595                 600                 605

Trp Ala Ala Glu Leu Pro Phe Pro Ala Asp Ser Ser Asp Pro Ala Ser
610                 615                 620

Gln Leu Ser Tyr Ser Gln Glu Val Gly Gly Pro Phe Lys Thr Pro Ile
625                 630                 635                 640

Lys Glu Thr Leu Pro Ile Ser Ser Thr Pro Ser Lys Ser Val Leu Pro
                645                 650                 655

Arg Thr Pro Glu Ser Trp Arg Leu Thr Pro Pro Ala Lys Val Gly Gly
            660                 665                 670

Leu Asp Phe Ser Pro Val Gln Thr Ser Gln Gly Ala Ser Asp Pro Leu
            675                 680                 685

Pro Asp Pro Leu Gly Leu Met Asp Leu Ser Thr Thr Pro Leu Gln Ser
            690                 695                 700

Ala Pro Pro Leu Glu Ser Pro Gln Arg Leu Leu Ser Ser Glu Pro Leu
705                 710                 715                 720

Asp Leu Ile Ser Val Pro Phe Gly Asn Ser Ser Pro Ser Asp Ile Asp
                725                 730                 735

Val Pro Lys Pro Gly Ser Pro Glu Pro Gln Val Ser Gly Leu Ala Ala
            740                 745                 750
```

```
Asn Arg Ser Leu Thr Glu Gly Leu Val Leu Asp Thr Met Asn Asp Ser
            755                 760                 765

Leu Ser Lys Ile Leu Leu Asp Ile Ser Phe Pro Gly Leu Asp Glu Asp
770             775                 780

Pro Leu Gly Pro Asp Asn Ile Asn Trp Ser Gln Phe Ile Pro Glu Leu
785             790                 795                 800

Gln

<210> SEQ ID NO 3
<211> LENGTH: 748
<212> TYPE: PRT
<213> ORGANISM: Homo sapiens

<400> SEQUENCE: 3

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
50                  55                  60

Ile Asn His Pro Thr Met Pro Asn Thr Gln Val Val Ala Ile Pro Asn
65              70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
130                 135                 140

Pro Ala Ala Arg Asp Val Asn Leu Pro Arg Pro Pro Gly Ala Leu Cys
145             150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
210                 215                 220

Pro Ser Ala Ser Trp Gln Asn Ser Val Ser Glu Arg Pro Pro Tyr Ser
225             230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
290                 295                 300

Val Ser Phe Trp Thr Ile His Pro Ser Ala Asn Arg Tyr Leu Thr Leu
305             310                 315                 320
```

```
Asp Gln Val Phe Lys Gln Gln Lys Arg Pro Asn Pro Glu Leu Arg Arg
            325                 330                 335

Asn Met Thr Ile Lys Thr Glu Leu Pro Leu Gly Ala Arg Arg Lys Met
        340                 345                 350

Lys Pro Leu Leu Pro Arg Val Ser Ser Tyr Leu Val Pro Ile Gln Phe
            355                 360                 365

Pro Val Asn Gln Ser Leu Val Leu Gln Pro Ser Val Lys Val Pro Leu
370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Glu Lys Leu Leu Phe Gly
            420                 425                 430

Glu Gly Phe Ser Pro Leu Leu Pro Val Gln Thr Ile Lys Glu Glu Glu
                435                 440                 445

Ile Gln Pro Gly Glu Glu Met Pro His Leu Ala Arg Pro Ile Lys Val
        450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
        515                 520                 525

Ser Arg Arg Lys Gln His Leu Leu Pro Pro Cys Val Asp Glu Pro Glu
530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
            565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
        595                 600                 605

Trp Arg Leu Thr Pro Pro Ala Lys Val Gly Gly Leu Asp Phe Ser Pro
        610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
            675                 680                 685

Ser Pro Glu Pro Gln Val Ser Gly Leu Ala Ala Asn Arg Ser Leu Thr
        690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
```

<210> SEQ ID NO 4
<211> LENGTH: 763
<212> TYPE: PRT
<213> ORGANISM: Homo sapiens

<400> SEQUENCE: 4

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365
```

```
Pro Leu Leu Pro Arg Val Ser Ser Tyr Leu Val Pro Ile Gln Phe Pro
    370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Leu Leu Ala Glu Gly Ile Ala Pro
            420                 425                 430

Leu Ser Ala Gly Pro Gly Lys Glu Lys Leu Leu Phe Gly Glu
        435                 440                 445

Gly Phe Ser Pro Leu Leu Pro Val Gln Thr Ile Lys Glu Glu Ile
    450                 455                 460

Gln Pro Gly Glu Glu Met Pro His Leu Ala Arg Pro Ile Lys Val Glu
465                 470                 475                 480

Ser Pro Pro Leu Glu Glu Trp Pro Ser Pro Ala Pro Ser Phe Lys Glu
                485                 490                 495

Glu Ser Ser His Ser Trp Glu Asp Ser Ser Gln Ser Pro Thr Pro Arg
                500                 505                 510

Pro Lys Lys Ser Tyr Ser Gly Leu Arg Ser Pro Thr Arg Cys Val Ser
            515                 520                 525

Glu Met Leu Val Ile Gln His Arg Glu Arg Arg Glu Arg Ser Arg Ser
530                 535                 540

Arg Arg Lys Gln His Leu Leu Pro Pro Cys Val Asp Glu Pro Glu Leu
545                 550                 555                 560

Leu Phe Ser Glu Gly Pro Ser Thr Ser Arg Trp Ala Ala Glu Leu Pro
                565                 570                 575

Phe Pro Ala Asp Ser Ser Asp Pro Ala Ser Gln Leu Ser Tyr Ser Gln
            580                 585                 590

Glu Val Gly Gly Pro Phe Lys Thr Pro Ile Lys Glu Thr Leu Pro Ile
        595                 600                 605

Ser Ser Thr Pro Ser Lys Ser Val Leu Pro Arg Thr Pro Glu Ser Trp
    610                 615                 620

Arg Leu Thr Pro Pro Ala Lys Val Gly Gly Leu Asp Phe Ser Pro Val
625                 630                 635                 640

Gln Thr Ser Gln Gly Ala Ser Asp Pro Leu Pro Asp Pro Leu Gly Leu
                645                 650                 655

Met Asp Leu Ser Thr Thr Pro Leu Gln Ser Ala Pro Pro Leu Glu Ser
            660                 665                 670

Pro Gln Arg Leu Leu Ser Ser Glu Pro Leu Asp Leu Ile Ser Val Pro
        675                 680                 685

Phe Gly Asn Ser Ser Pro Ser Asp Ile Asp Val Pro Lys Pro Gly Ser
    690                 695                 700

Pro Glu Pro Gln Val Ser Gly Leu Ala Ala Asn Arg Ser Leu Thr Glu
705                 710                 715                 720

Gly Leu Val Leu Asp Thr Met Asn Asp Ser Leu Ser Lys Ile Leu Leu
                725                 730                 735

Asp Ile Ser Phe Pro Gly Leu Asp Glu Asp Pro Leu Gly Pro Asp Asn
            740                 745                 750

Ile Asn Trp Ser Gln Phe Ile Pro Glu Leu Gln
        755                 760

<210> SEQ ID NO 5
<211> LENGTH: 155
<212> TYPE: PRT
```

-continued

<213> ORGANISM: Homo sapiens

<400> SEQUENCE: 5

```
Met Lys Val Ala Ser Gly Ser Thr Ala Thr Ala Ala Gly Pro Ser
1               5                   10                  15

Cys Ala Leu Lys Ala Gly Lys Thr Ala Ser Gly Ala Gly Glu Val Val
            20                  25                  30

Arg Cys Leu Ser Glu Gln Ser Val Ala Ile Ser Arg Cys Ala Gly Gly
        35                  40                  45

Ala Gly Ala Arg Leu Pro Ala Leu Leu Asp Glu Gln Gln Val Asn Val
    50                  55                  60

Leu Leu Tyr Asp Met Asn Gly Cys Tyr Ser Arg Leu Lys Glu Leu Val
65                  70                  75                  80

Pro Thr Leu Pro Gln Asn Arg Lys Val Ser Lys Val Glu Ile Leu Gln
                85                  90                  95

His Val Ile Asp Tyr Ile Arg Asp Leu Gln Leu Glu Leu Asn Ser Glu
            100                 105                 110

Ser Glu Val Gly Thr Pro Gly Gly Arg Gly Leu Pro Val Arg Ala Pro
        115                 120                 125

Leu Ser Thr Leu Asn Gly Glu Ile Ser Ala Leu Thr Ala Glu Ala Ala
    130                 135                 140

Cys Val Pro Ala Asp Asp Arg Ile Leu Cys Arg
145                 150                 155
```

<210> SEQ ID NO 6
<211> LENGTH: 149
<212> TYPE: PRT
<213> ORGANISM: Homo sapiens

<400> SEQUENCE: 6

```
Met Lys Val Ala Ser Gly Ser Thr Ala Thr Ala Ala Gly Pro Ser
1               5                   10                  15

Cys Ala Leu Lys Ala Gly Lys Thr Ala Ser Gly Ala Gly Glu Val Val
            20                  25                  30

Arg Cys Leu Ser Glu Gln Ser Val Ala Ile Ser Arg Cys Ala Gly Gly
        35                  40                  45

Ala Gly Ala Arg Leu Pro Ala Leu Leu Asp Glu Gln Gln Val Asn Val
    50                  55                  60

Leu Leu Tyr Asp Met Asn Gly Cys Tyr Ser Arg Leu Lys Glu Leu Val
65                  70                  75                  80

Pro Thr Leu Pro Gln Asn Arg Lys Val Ser Lys Val Glu Ile Leu Gln
                85                  90                  95

His Val Ile Asp Tyr Ile Arg Asp Leu Gln Leu Glu Leu Asn Ser Glu
            100                 105                 110

Ser Glu Val Gly Thr Pro Gly Gly Arg Gly Leu Pro Val Arg Ala Pro
        115                 120                 125

Leu Ser Thr Leu Asn Gly Glu Ile Ser Ala Leu Thr Ala Glu Val Arg
    130                 135                 140

Ser Arg Ser Asp His
145
```

<210> SEQ ID NO 7
<211> LENGTH: 464
<212> TYPE: PRT
<213> ORGANISM: Homo sapiens

<400> SEQUENCE: 7

```
Met Ser Leu His Phe Leu Tyr Tyr Cys Ser Glu Pro Thr Leu Asp Val
1               5                   10                  15

Lys Ile Ala Phe Cys Gln Gly Phe Asp Lys Gln Val Asp Val Ser Tyr
            20                  25                  30

Ile Ala Lys His Tyr Asn Met Ser Lys Ser Lys Val Asp Asn Gln Phe
        35                  40                  45

Tyr Ser Val Glu Val Gly Asp Ser Thr Phe Thr Val Leu Lys Arg Tyr
    50                  55                  60

Gln Asn Leu Lys Pro Ile Gly Ser Gly Ala Gln Gly Ile Val Cys Ala
65                  70                  75                  80

Ala Tyr Asp Ala Val Leu Asp Arg Asn Val Ala Ile Lys Lys Leu Ser
                85                  90                  95

Arg Pro Phe Gln Asn Gln Thr His Ala Lys Arg Ala Tyr Arg Glu Leu
            100                 105                 110

Val Leu Met Lys Cys Val Asn His Lys Asn Ile Ile Ser Leu Leu Asn
        115                 120                 125

Val Phe Thr Pro Gln Lys Thr Leu Glu Glu Phe Gln Asp Val Tyr Leu
    130                 135                 140

Val Met Glu Leu Met Asp Ala Asn Leu Cys Gln Val Ile Gln Met Glu
145                 150                 155                 160

Leu Asp His Glu Arg Met Ser Tyr Leu Leu Tyr Gln Met Leu Cys Gly
                165                 170                 175

Ile Lys His Leu His Ser Ala Gly Ile Ile His Arg Asp Leu Lys Pro
            180                 185                 190

Ser Asn Ile Val Val Lys Ser Asp Cys Thr Leu Lys Ile Leu Asp Phe
        195                 200                 205

Gly Leu Ala Arg Thr Ala Gly Thr Ser Phe Met Met Thr Pro Tyr Val
    210                 215                 220

Val Thr Arg Tyr Tyr Arg Ala Pro Glu Val Ile Leu Gly Met Gly Tyr
225                 230                 235                 240

Lys Glu Asn Val Asp Ile Trp Ser Val Gly Cys Ile Met Gly Glu Met
                245                 250                 255

Val Arg His Lys Ile Leu Phe Pro Gly Arg Asp Tyr Ile Asp Gln Trp
            260                 265                 270

Asn Lys Val Ile Glu Gln Leu Gly Thr Pro Cys Pro Glu Phe Met Lys
        275                 280                 285

Lys Leu Gln Pro Thr Val Arg Asn Tyr Val Glu Asn Arg Pro Lys Tyr
    290                 295                 300

Ala Gly Leu Thr Phe Pro Lys Leu Phe Pro Asp Ser Leu Phe Pro Ala
305                 310                 315                 320

Asp Ser Glu His Asn Lys Leu Lys Ala Ser Gln Ala Arg Asp Leu Leu
                325                 330                 335

Ser Lys Met Leu Val Ile Asp Pro Ala Lys Arg Ile Ser Val Asp Asp
            340                 345                 350

Ala Leu Gln His Pro Tyr Ile Asn Val Trp Tyr Asp Pro Ala Glu Val
        355                 360                 365

Glu Ala Pro Pro Pro Gln Ile Tyr Asp Lys Gln Leu Asp Glu Arg Glu
    370                 375                 380

His Thr Ile Glu Glu Trp Lys Glu Leu Ile Tyr Lys Glu Val Met Asn
385                 390                 395                 400

Ser Glu Glu Lys Thr Lys Asn Gly Val Val Lys Gly Gln Pro Ser Pro
                405                 410                 415
```

-continued

```
Ser Gly Ala Ala Val Asn Ser Ser Glu Ser Leu Pro Pro Ser Ser Ser
            420                 425                 430

Val Asn Asp Ile Ser Ser Met Ser Thr Asp Gln Thr Leu Ala Ser Asp
        435                 440                 445

Thr Asp Ser Ser Leu Glu Ala Ser Ala Gly Pro Leu Gly Cys Cys Arg
    450                 455                 460
```

THERAPEUTIC GENE COCKTAIL FOR HEART REGENERATION

RELATED APPLICATIONS

This Application is a national stage filing under 35 U.S.C. § 371 of International Application No. PCT/US2016/028249, entitled "A THERAPEUTIC GENE COCKTAIL FOR HEART REGENERATION", filed Apr. 19, 2016, which claims the benefit under 35 U.S.C. § 119(e) of U.S. Provisional Application No. 62/149,854, filed on Apr. 20, 2015, entitled "A THERAPEUTIC GENE COCKTAIL FOR HEART REGENERATION", the entire contents of each of which are incorporated by reference herein.

BACKGROUND OF THE INVENTION

Heart regeneration has been a long-standing challenge due to the low proliferative ability of mammalian adult cardiomyocyte (CM) cells. CMs execute their final round of DNA synthesis and karyokinesis, become binucleated, and subsequently exit the cell cycle during the first week after birth. Although the remnants CMs possess certain degree of proliferation after a cardiac damage, the efficiency is low. Naqvi et al., Cell 157(4):795-807; 2014.

It was reported that somatic cells can be reprogrammed back to a pluripotent cell state similar to embryonic stem cells (ESCs) with high proliferative ability. Takahashi et al., Cell 126(4):663-676; 2006. Such reprogrammed cells are known as induced pluripotent stem cells (iPS cells or iPSCs). However, evidence in the art showed that CMs do have the potential to be reprogrammed. Xu et al., Cell Res. 22(1):142-154. Also, little was known regarding the detail mechanism or function at different time points for CMs to re-enter cell cycle.

SUMMARY OF THE INVENTION

The present disclosure is based on the unexpected discoveries of the critical time point for cardiomyocyte reprogramming and a gene set, including FoxM1, Id1, and JNK3, that plays important roles in cardiomyocyte proliferation. Surprisingly, it was observed that enhancers or inhibitors of the gene set described herein successfully promoted not only the proliferation of neonatal cardiomyocytes, but also the proliferation of adult cardiomyocytes in heart damages. In particular, a combination of a FoxM1 enhancer, an Id1 enhancer, and a JNK3 inhibitor successfully achieved this goal.

Accordingly, the present disclosure provides a method for promoting heart regeneration or heart cell proliferation, the method comprising administering to a subject in need thereof an effective amount of a combination comprising at least two of the following: (i) a FoxM1 enhancer, (ii) an Id1 enhancer, and (iii) a JNK3 inhibitor. The combination may contain (i) and (ii), (i) and (iii), (ii) and (iii). In some examples, the combination may contain all of (i)-(iii).

In some embodiments, the FoxM1 enhancer is a FoxM1 polypeptide or an expression vector for producing the FoxM1 polypeptide. In some embodiments, the Id1 enhancer is an Id1 polypeptide or an expression vector for producing the Id1 polypeptide. Alternatively or in addition, the JNK3 inhibitor is a JNK3-specific shRNA.

In any of the methods described herein, the administering step is performed by delivering to the subject one or more expression vectors for producing the FoxM1 polypeptide, the Id1 polypeptide, and the JNK3-specific shRNA. In some embodiments, the one or more expression vectors are viral vectors (e.g., adenoviral vectors or adeno-associated viral vectors) or non-viral vectors.

The subject to be treated by the method described herein can be a human patient having, suspected of having, or at risk for myocardial infarction. In some examples, the combination is administered to a site having or suspected of having a heart degenerative disorder. In some examples the subject is a neonate. In some examples, the subject is an adult.

In another aspect, the present disclosure provides a kit for promoting heart regeneration, the kit comprising at least two of: (i) a FoxM1 enhancer as described herein; (ii) an Id1 enhancer as described herein; and (iii) a JNK3 inhibitor as described herein. The kit may comprise any of the combinations of (i) to (iii), for example, all of (i)-(iii). In some examples, the kit comprises expression vectors for producing the FoxM1 polypeptide, the Id1 polypeptide, and/or the JNK3-specific shRNA. The expression vectors may be viral vectors (e.g., adenoviral vectors or adeno-associated viral vectors) or non-viral vectors.

In any of the kits described herein, the kit may further comprise instructions for administering the FoxM1 enhancer, the Id1 enhancer, and the JNK3 inhibitor to a subject for promoting heart regeneration or heart cell proliferation.

In yet another aspect, the present disclosure features a method for promoting cardiomyocyte proliferation and differentiation, the method comprising culturing cardiomyocyte cells in the presence of at least two of the following: (i) a FoxM1 enhancer; (ii) an Id1 enhancer; and (iii) a JNK3 inhibitor. The method may further comprise delivering the cultured cardiomyocyte cells to a subject in need thereof. Any of the FoxM1 enhancer, Id1 enhancer, and JNK3 inhibitor as described herein can be used in this method. In some embodiments, the cardiomyocyte cells are cultured in the presence of all of (i)-(iii).

The subject to be treated by the method described herein may be a human patient having, suspected of having, or being at risk for a heart degenerative disorder. In some embodiments, the cardiomyocyte cells are autologous. In other embodiments, the cardiomyocyte cells are allogenic. In some embodiments, the subject is a neonate. In some embodiments, the subject is an adult.

Also within the scope of the present disclosure are pharmaceutical compositions for use in promoting heart regeneration or heart cell proliferation, the composition comprises a combination comprising at least two of i) a FoxM1 enhancer; (ii) an Id1 enhancer; and (iii) a JNK3 inhibitor; and a pharmaceutically acceptable carrier. Alternatively, the pharmaceutical composition comprises cardiomyocyte cells cultured in the presence of the combination. The present disclosure further provides any of the combination of FoxM1 enhancer, Id1 enhancer, and/or JNK3 inhibitor, or cardiomyocyte cells cultured in the presence of such a combination for use in manufacturing a medicament for promoting heart regeneration.

The details of one or more embodiments of the disclosure are set forth in the description below. Other features or advantages of the present disclosure will be apparent from the following drawings and detailed description of several embodiments, and also from the appended claims.

BRIEF DESCRIPTION OF THE DRAWINGS

FIG. 1A shows the experimental procedure. FIG. 1B shows morphologies at different time points during CM reprogramming. FIG. 1C shows gene ontological analysis during CM reprogramming.

FIG. 2A shows up-regulated gene selection. FIG. 2B shows combined down-regulated gene selection. FIG. 2C shows ideal triple combination of FoxM1, Id1, and Jnk3 for CM proliferation.

FIG. 3A shows the experimental procedure. FIG. 3B depicts higher value of heart-to-body weight. FIG. 3C depicts the higher percentage of the Ki-67 or H3P positive population.

FIG. 4A shows the experimental procedure for CM proliferation after injury. FIG. 4B shows a higher percentage of the Ki-67 or H3P positive population. FIG. 4C shows the experimental procedure for improvement of heart function after injury. FIG. 4D shows improvement of heart function by echocardiography FIG. 4E shows improvement of heart function by fibrosis assay.

FIG. 5A shows the timeline followed for adult reprogrammable mice administered doxycycline or control mice. FIG. 5B shows the RNA expression ratio of Oct4, FoxM1, Id1, or Jnk3 in doxycycline-injected versus control adult CMs isolated from reprogrammable OSKM mice. FIG. 5C shows the quantification of $H3P^+$ and $cTnI^+$ population % in the heart tissue sections from control or doxycycline injected mice. FIG. 5D shows the timeline followed for adult mice administered the adeno-Ctrl or adeno-FIJs. FIG. 5E shows the quantification of $H3P^+$ and $cTnI^+$ population % in the heart tissue sections from adeno-Ctrl or adeno-FIJs injected mice. Data are represented as mean±SEM. Sample size is indicated in the bar chart. *, P<0.05, and ***, P<0.001.

DETAILED DESCRIPTION OF THE INVENTION

Figure 1A:
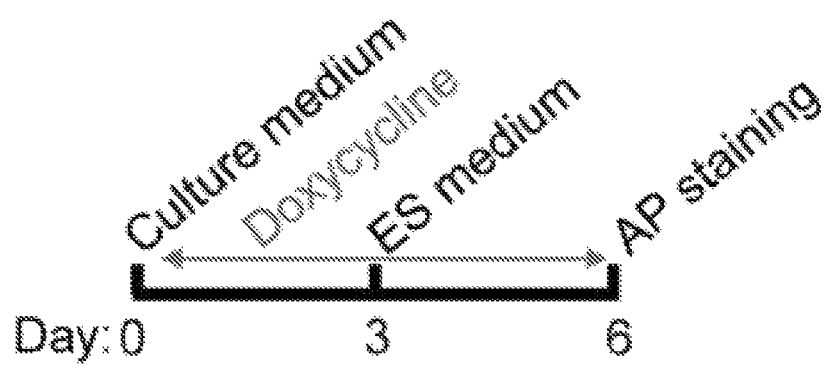
FIGS. 1A-1C are diagrams showing the proliferation of cardiomyocytes (CM) at reprogramming day 2 based on the gene ontological analysis of DNA microarray results.

The present disclosure is based at least in part on the identification of the specific time point for CM proliferation at reprogramming day 2 and the identification of the involvement of FoxM1, Id1, and/or JNK3 genes in CM proliferation. Unexpectedly, gene cocktails, including double or triple combinations of FoxM1, Id1, and Jnk3-shRNA (a JNK3 inhibitor), were found to efficiently enhance CM proliferation in vitro in both neonatal and adult mice. The present disclosure also shows that the triple combination of FoxM1, Id1, and Jnk3-shRNA was effective for heart development and regeneration after injury in vivo.

Accordingly, the present disclosure features methods for promoting CM cell proliferation (either in vivo or in vitro), using a combination of at least two of the following: (i) a FoxM1 enhancer, (ii) an Id1 enhancer, and (iii) a JNK3 inhibitor.

I. FoxM1, Id1, and JNK3 Enhancers or Inhibitors

One aspect of the present disclosure relates to combinations of at least two of (i) a FoxM1 enhancer, (ii) an Id1 enhancer, and (iii) a JNK3 inhibitor.

As used herein, an enhancer of a specific gene/protein refers to any agent that enhances the level or activity of the protein product encoded by the gene (gene product) in a target cell (e.g., a cardiomyocyte). An enhancer of the gene may be a nucleic acid (e.g., an expression vector) which produces the protein product encoded by the gene when introduced into the target cell. The enhancer may also be a polypeptide of the gene product that exhibits the same bioactivity as the gene product (e.g., the full-length gene product, a functional fragment thereof, or a fusion protein comprising a functional fragment of the gene product). In other examples, the enhancer may be an agent (e.g., a nucleic acid, a polypeptide, or a small molecule) that activates the expression of the gene or improves the bioactivity of the gene product. In some embodiments, an enhance may improve the activity of the gene product by at least 10%, 20%, 50%, 100%, 2-fold, 5-fold, 10-fold, 50-fold, 100 fold, or 1,000-fold as compared to the absence of the enhancer.

As used herein, an inhibitor of a target gene/protein refers to any agent that reduces the level or activity of the protein product encoded by the target gene in a target cell (e.g., a cardiomyocyte). An inhibitor of the gene may be a nucleic acid, a polypeptide, or a small molecule that suppresses the expression of the gene or inhibits the bioactivity of the gene product. For example, an inhibitor can be an antisense oligonucleotide or an interfering RNA that targets one or more specific sites of the target gene or its mRNA so as to block gene transcription or protein translation. In some embodiments, an inhibitor may suppress the activity of the gene product by at least 10%, 20%, 30%, 40%, 50%, 60%, 70%, 80%, 90%, or at least 95% as compared to the absence of the inhibitor. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. The oligonucleotide inhibitors (including antisense oligonucleotides and interfering RNAs such as shRNAs) can be about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-O sugar modifications well known in the art. In some instances, the oligonucleotides may contain one or more locked nucleic acids (LNAs). In other examples, an inhibitor can be an antibody (e.g., full-length or an antigen-binding fragment thereof), which neutralizes the activity of the target protein.

(i) FoxM1 Enhancers

The FoxM1 enhancer described herein is an agent that enhances the level or activity of FoxM1 in a target cell such as in cardiomyocyte. FoxM1 (Forkhead box M1) is a member of the FOX transcription factor family. The human protein (e.g., NP_973732.1) is encoded by the FOXM1 gene (e.g., Gene ID number 2305; Genomic reference sequence NG_029590.1). There are three isoforms of FoxM1, isoform A, isoform B, and isoform C, all of which are within the scope of the present disclosure. In some embodiments, the FoxM1 enhancer disclosed herein is a FoxM1 polypeptide, which is a protein possessing the same biological activity as FoxM1. A FoxM1 polypeptide can be the full-length FoxM1 protein, a functional fragment thereof, or a fusion protein comprising a functional fragment of FoxM1. FoxM1 contains 3 functional domains including the N-terminal auto-inhibitory domain, the fork-head family DNA-binding domain, and the C-terminal transactivation domain. The N-terminal auto-inhibitory domain (residue 1-232) is regulated by cyclin A, such that FoxM1 converts to the active form at G2/M phase during cell cycle. The LXL fragment (residue 641-748) in the C-terminal domain of FoxM1 is targeted binding by N-terminal domain for auto-inhibition (Laoukili et al., 2008; Park et al., 2008). After deletion of these 2 fragments, the resultant FoxM1 fragment is constitutively active through the whole cell cycle. Thus, in some examples, the functional fragment of FoxM1 comprises the residue 232-641 of FoxM1.

In some embodiments, a FoxM1 poly peptide is a naturally-occurring FoxM1 polypeptide from a suitable source (e.g., from a human, monkey, mouse, or rat). For example a FoxM1 polypeptide may be a FoxM1 polypeptide form a human or a mouse (e.g., a C57BL/6 mouse). It should be appreciated that a FoxM1 polypeptide can be any isoform of FoxM1 (e.g., a naturally-occurring isoform of FoxM1). For example, a FoxM1 may be an isoform A, an isoform B, or an isoform C of human FoxM1. Additional isoforms of FoxM1 are known in the art and are within the scope of this disclosure. In some embodiments, a FoxM1 polypeptide comprises an amino acid sequence as set forth in any one of SEQ ID NOs: 2-4, or a functional fragment thereof such as those known in the art and/or disclosed herein (e.g., the underlined fragments of SEQ ID NOs:2-4).

FoxM1A (gi|42544167|ref|NP_973731.1| forkhead box protein M1 isoform 1 [*Homo sapiens*]):

```
                                              (SEQ ID NO: 2)
MKTSPRRPLILKRRRLPLPVQNAPSETSEEEPKRSPAQQESNQAEASKEV

AESNSCKFPAGIKIINHPTMPNTQVVAIPNNANIHSIITALTAKGKESGS

SGPNKFILISCGGAPTQPPGLRPQTQTSYDAKRTEVTLETLGPKPAARDV

NLPRPPGALCEQKRETCADGEAAGCTINNSLSNIQWLRKMSSDGLGSRSI

KQEMEEKENCHLEQRQVKVEEPSRPSASWQNSVSERPPYSYMAMIQFAIN

STERKRMTLKDIYTWIEDHFPYFKHIAKPGWKNSIRHNLSLHDMFVRETS

ANGKVSFWTIHPSANRYLTLDQVFKPLDPGSPQLPEHLESQQKRPNPELR

RNMTIKTELPLGARRKMKPLLPRVSSYLVPIQFPVNQSLVLQPSVKVPLP

LAASLMSSELARHSKRVRIAPKVFGEQVVFGYMSKFFSGDLRDFGTPITS

LFNFIFLCLSVLLAEEGIAPLSSAGPGKEEKLLFGEGFSPLLPVQTIKEE

EIQPGEEMPHLARPIKVESPPLEEWPSPAPSFKEESSHSWEDSSQSPTPR

PKKSYSGLRSPTRCVSEMLVIQHRERRERSRSRRKQHLLPPCVDEPELLF

SEGPSTSRWAAELPFPADSSDPASQLSYSQEVGGPFKTPIKETLPISSTP

SKSVLPRTPESWRLTPPAKVGGLDFSPVQTSQGASDPLPDPLGLMDLSTT

PLQSAPPLESPQRLLSSEPLDLISVPFGNSSPSDIDVPKPGSPEPQVSGL

AANRSLTEGLVLDTMNDSLSKILLDISFPGLDEDPLGPDNINWSQFIPEL

Q
```

FOXM1B (gi|42544161|ref|NP_973732.1| forkhead box protein M1 isoform 3 [*Homo sapiens*]):

```
                                              (SEQ ID NO: 3)
MKTSPRRPLILKRRRLPLPVQNAPSETSEEEPKRSPAQQESNQAEASKEV

AESNSCKFPAGIKIINHPTMPNTQVVAIPNNANIHSIITALTAKGKESGS

SGPNKFILISCGGAPTQPPGLRPQTQTSYDAKRTEVTLETLGPKPAARDV

NLPRPPGALCEQKRETCADGEAAGCTINNSLSNIQWLRKMSSDGLGSRSI

KQEMEEKENCHLEQRQVKVEEPSRPSASWQNSVSERPPYSYMAMIQFAIN

STERKRMTLKDIYTWIEDHFPYFKHIAKPGWKNSIRHNLSLHDMFVRETS

ANGKVSFWTIHPSANRYLTLDQVFKQQKRPNPELRRNMTIKTELPLGARR

KMKPLLPRVSSYLVPIQFPVNQSLVLQPSVKVPLPLAASLMSSELARHSK

RVRIAPKVLLAEEGIAPLSSAGPGKEEKLLFGEGFSPLLPVQTIKEEEIQ

PGEEMPHLARPIKVESPPLEEWPSPAPSFKEESSHSWEDSSQSPTPRPKK

SYSGLRSPTRCVSEMLVIQHRERRERSRSRRKQHLLPPCVDEPELLFSEG

PSTSRWAAELPFPADSSDPASQLSYSQEVGGPFKTPIKETLPISSTPSKS

VLPRTPESWRLTPPAKVGGLDFSPVQTSQGASDPLPDPLGLMDLSTTPLQ

SAPPLESPQRLLSSEPLDLISVPFGNSSPSDIDVPKPGSPEPQVSGLAAN

RSLTEGLVLDTMNDSLSKILLDISFPGLDEDPLGPDNINWSQFIPELQ
```

FOXM1C (gi|42544165|ref|NP_068772.2| forkhead box protein M1 isoform 2 [*Homo sapiens*]):

```
                                              (SEQ ID NO: 4)
MKTSPRRPLILKRRRLPLPVQNAPSETSEEEPKRSPAQQESNQAEASKEV

AESNSCKFPAGIKIINHPTMPNTQVVAIPNNANIHSIITALTAKGKESGS

SGPNKFILISCGGAPTQPPGLRPQTQTSYDAKRTEVTLETLGPKPAARDV

NLPRPPGALCEQKRETCADGEAAGCTINNSLSNIQWLRKMSSDGLGSRSI

KQEMEEKENCHLEQRQVKVEEPSRPSASWQNSVSERPPYSYMAMIQFAIN

STERKRMTLKDIYTWIEDHFPYFKHIAKPGWKNSIRHNLSLHDMFVRETS

ANGKVSFWTIHPSANRYLTLDQVFKPLDPGSPQLPEHLESQQKRPNPELR

RNMTIKTELPLGARRKMKPLLPRVSSYLVPIQFPVNQSLVLQPSVKVPLP

LAASLMSSELARHSKRVRIAPKVLLAEEGIAPLSSAGPGKEEKLLFGEGF

SPLLPVQTIKEEEIQPGEEMPHLARPIKVESPPLEEWPSPAPSFKEESSH

SWEDSSQSPTPRPKKSYSGLRSPTRCVSEMLVIQHRERRERSRSRRKQHL

LPPCVDEPELLFSEGPSTSRWAAELPFPADSSDPASQLSYSQEVGGPFKT

PIKETLPISSTPSKSVLPRTPESWRLTPPAKVGGLDFSPVQTSQGASDPL

PDPLGLMDLSTTPLQSAPPLESPQRLLSSEPLDLISVPFGNSSPSDIDVP

KPGSPEPQVSGLAANRSLTEGLVLDTMNDSLSKILLDISFPGLDEDPLGP

DNINWSQFIPELQ
```

The underlined fragment refers to the constitutively active form of FoxM1. Additional human FOXM1B isoforms include NP_001230017.1 and NP_001230018.1.

The disclosure contemplates variants of FoxM1 polypeptides, such as any polypeptide that is not identical to, but shares a degree of homology with a FoxM1 polypeptide from an organism (e.g., from a human, monkey, mouse, or rat) and possesses similar biological activity as the naturally-occurring counterpart. As used herein, the term "homologous" refers to the overall relatedness between nucleic acids or polypeptides. In some embodiments, polypeptides are considered to be "homologous" to one another if their sequences are at least 60%, at least 65%, at least 70%, at least 75%, at least 80%, at least 85%, at least 90%, at least 95%, or at least 99% identical. The term "homologous" refers to a comparison between at least two sequences (e.g., amino acid sequences). In some embodiments, a FoxM1 polypeptide comprises an amino acid sequence that is at least 70%, at least 75%, at least 80%, at least 85%, at least 90%, at least 92%, at least 95%, at least 96%, at least 97%, at least 98%, at least 99%, or at least 99.5% identical to the amino acid sequence as set forth in any one of SEQ ID NOs: 2-4).

Calculating the percent identity of two sequences, for example polypeptide sequences, can be performed by aligning the two sequences for optimal comparison purposes (e.g., gaps can be introduced in one or both of a first and second nucleic acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding polypeptide positions are then compared. When a position in the first sequence is occupied by the same amino acid as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. Techniques for determining identity are codified in publicly available computer programs. Exemplary computer software to determine homology between two sequences include, but are not limited to, BLASTP, ClustalW, Clustal Omega, and Base-By-Base.

In some embodiments, a FoxM1 polypeptide is a functional fragment of a FoxM1 polypeptide from an organism (e.g., from a human, monkey, mouse, or rat), or homologous polypeptide thereof. As used herein a "FoxM1 functional fragment" refers to a portion of a FoxM1 polypeptide, or a portion of a protein homologous to a FoxM1 polypeptide and possesses similar biological activity as the counterpart FoxM1 polypeptide. In some embodiments, a FoxM1 fragment modulates expression of a gene (e.g., Plk1, cyclin B2, NeK2, or CENPF), which may be determined by routine methods known in the art. In some embodiments, a FoxM1 fragment increases cell proliferation, which may be determined by any suitable method, for example, by determining an expression level of H3P. In some embodiments, a FoxM1 fragment is constitutively active, meaning that the FoxM1 fragment is active throughout a cell cycle, for example, by removing one or more auto-inhibitory domains.

In some embodiments, a FoxM1 fragment comprises a C-terminal portion of a FoxM1 polypeptide. For example, the FoxM1 fragment for use in the methods described herein may comprise (e.g., consists of) amino acids 232-694 of SEQ ID NO: 2, or a polypeptide homologous thereto. In some embodiments, a FoxM1 fragment comprises amino acids 232-641 of SEQ ID NO: 3, or a polypeptide homologous thereto. In some embodiments, a FoxM1 fragment comprises amino acids 232-656 of SEQ ID NO: 4, or a polypeptide homologous thereto.

In other embodiments, the FoxM1 enhancer disclosed herein is a nucleic acid, such as an expression vector, that comprises a nucleotide sequence encoding any of the FoxM1 polypeptides described herein. The encoding nucleotide sequence is in operable linkage to a suitable promoter. When introduced into a target cell (e.g., a cardiomyocyte cell), the nucleic acid produces the FoxM1 polypeptide.

In yet other embodiments, the FoxM1 enhancer disclosed herein is an agent (e.g., a small molecule) that enhances the expression of the FOXM1 gene or activates the activity of the FoxM1 protein. Examples include, but are not limited to, AMPK (Sengupta et al. 2012, Circ Res.) Osteopontin (Xie et al., 2014, Int J Mol Sci.) CXCL12 (Wang et al. 2013, BBRC) and TNF-α (Xia et al. 2012, Oncogen).

(ii) Id1 Enhancers

The Id1 (or DNA-binding protein inhibitor ID-1) enhancer described herein can be an agent that enhances the level or activity of Id1 in a target cell such as in cardiomyocyte. Id1 is a helix-loop-helix (HLH) protein that can form heterodimers with members of the basic HLH family of transcription factors. The human protein (e.g., NP_002156.2 and NP_851998.1) is encoded by the ID1 gene (e.g., Gene ID number 3397; Genomic reference sequence NG_029639). In some embodiments, the Id1 enhancer disclosed herein is an Id1 polypeptide, which is a protein possessing the same biological activity as Id1. An Id1 polypeptide can be the full-length Id1 protein, a functional fragment thereof, or a fusion protein comprising a functional fragment of Id1.

In some embodiments, a Id1 poly peptide is a naturally-occurring Id1 polypeptide from a suitable source (e.g., from a human, monkey, mouse, or rat). For example an Id1 polypeptide may be an Id1 polypeptide form a human or a mouse (e.g., a C57BL/6 mouse). It should be appreciated that an Id1 polypeptide can be any isoform of Id1. For example, an Id1 may be an isoform A, or an isoform B of human Id1. Additional isoforms of Id1 are known in the art and are within the scope of this disclosure. In some embodiments, an Id1 polypeptide comprises an amino acid sequence as set forth in any one of SEQ ID NOs: 5-6.

Id1 isoform A (gi|31317299|ref|NP_002156.2| DNA-binding protein inhibitor ID-1 isoform a [*Homo sapiens*]):

```
                                        (SEQ ID NO: 5)
MKVASGSTATAAAGPSCALKAGKTASGAGEVVRCLSEQSVAISRCAGGAG

ARLPALLDEQQVNVLLYDMNGCYSRLKELVPTLPQNRKVSKVEILQHVID

YIRDLQLELNSESEVGTPGGRGLPVRAPLSTLNGEISALTAEAACVPADD

RILCR
```

Id1 isoform B (gi|31317297|ref|NP_851998.1| DNA-binding protein inhibitor ID-1 isoform b [*Homo sapiens*]):

```
                                        (SEQ ID NO: 6)
MKVASGSTATAAAGPSCALKAGKTASGAGEVVRCLSEQSVAISRCAGGAG

ARLPALLDEQQVNVLLYDMNGCYSRLKELVPTLPQNRKVSKVEILQHVID

YIRDLQLELNSESEVGTPGGRGLPVRAPLSTLNGEISALTAEVRSRSDH
```

The disclosure contemplates variants of Id1 poly peptides, such as any polypeptide that is not identical to, but shares a degree of homology with an Id1 polypeptide from a naturally-occurring counterpart, e.g., that from human, monkey, mouse, or rat. In some embodiments, an Id1 polypeptide is a polypeptide that is homologous to a naturally-occurring Id1 polypeptide (e.g., from a human or mouse). In some embodiments, an Id1 polypeptide comprises an amino acid sequence that is at least 70%, at least 75%, at least 80%, at least 85%, at least 90%, at least 92%, at least 95%, at least 96%, at least 97%, at least 98%, at least 99%, or at least 99.5% identical to the amino acid sequence as set forth in any one of SEQ ID NOs: 5-6).

In some embodiments, an Id1 polypeptide is a functional fragment of an Id1 polypeptide, e.g., a naturally-occurring Id1 polypeptide and possesses similar biological activity as the counterpart Id1 polypeptide. In some embodiments, an Id1 fragment binds to a member of the basic HLH family of transcription factors. In some embodiments, an Id1 fragment bonds to and inhibits at least one function of a member of the basic HLH family of transcription factors. In some embodiments, an Id1 fragment modulates expression of a gene (e.g., TSP-1,), which may be determined by routine methods known in the art. In some embodiments, an Id1 fragment increases cell proliferation, which may be determined by any suitable method, for example, by determining an expression level of H3P.

In other embodiments, the Id1 enhancer disclosed herein is a nucleic acid, such as an expression vector, that comprises a nucleotide sequence encoding any of the Id1 polypeptides described herein. The encoding nucleotide sequence is in operably linkage to a suitable promoter. When introduced into a target cell (e.g., a cardiomyocyte cell), the nucleic acid produces the Id1 polypeptide.

In yet other embodiments, the Id1 enhancer disclosed herein is an agent (e.g., a small molecule, which typically has a molecular weight less than 5,000 kDa.) that enhances the expression of the Id1 gene or activates the activity of the Id1 protein. Examples include, but are not limited to, BMPs (Valdimarsdottir et al. 2002, Circulation), Leukemia inhibitory factor (LIF; Florholmen et al. 2004, Acta Physiol Scand) glucose or insulin (Wice et al., 2001, Diabetologia) LMP1 (Li et al., 2004, Oncogen), 5-aza-2'-deoxycytidine (DAC) or HDAC inhibitor trichostatin A (TSA) (Yu et al., 2008, Cell Prolif.)

(iii) JNK3 Inhibitors c-Jun N-terminal kinase 3 (JNK3), also known as Mitogen-activated protein kinase 10 (MAPK10), is a protein kinase of the MAPK family, which is activated by a variety of environmental stress and pro-inflammatory cytokines. An exemplary human JNK3 protein (e.g., NP_620448.1) is encoded by the MAPK10 gene (e.g., Gene ID number 5602; Genomic reference sequence NG_013325.2). Exemplary human JNK3 proteins include, but are not limited to isoform 1 (NP_620448.1), isoform 2 (NP_002744.1), isoform 3 (NP_620446.1), isoform 5 (NP_001304996.1), and isoform 6 (NP_001304997.1). An exemplary JNK3 amino acid sequence is set forth in SEQ ID NO: 7. It should be appreciated that JNK3 from other organisms (e.g., humans, monkeys, mice, and rats) including any naturally-occurring isoforms thereof, are within the scope of this disclosure.

JNK3, isoform 1 (gi|20986510|ref|NP_620448.1| mitogen-activated protein kinase 10 isoform 1 [*Homo sapiens*])

(SEQ ID NO: 7)
MSLHFLYYCSEPTLDVKIAFCQGFDKQVDVSYIAKHYNMSKSKVDNQFYS

VEVGDSTFTVLKRYQNLKPIGSGAQGIVCAAYDAVLDRNVAIKKLSRPFQ

-continued
NQTHAKRAYRELVLMKCVNHKNIISLLNVFTPQKTLEEFQDVYLVMELMD

ANLCQVIQMELDHERMSYLLYQMLCGIKHLHSAGIIHRDLKPSNIVVKSD

CTLKILDFGLARTAGTSFMMTPYVVTRYYRAPEVILGMGYKENVDIWSVG

CIMGEMVRHKILFPGRDYIDQWNKVIEQLGTPCPEFMKKLQPTVRNYVEN

RPKYAGLTFPKLFPDSLFPADSEHNKLKASQARDLLSKMLVIDPAKRISV

DDALQHPYINVWYDPAEVEAPPPQIYDKQLDEREHTIEEWKELIYKEVMN

SEEKTKNGVVKGQPSPSGAAVNSSESLPPSSSVNDISSMSTDQTLASDTD

SSLEASAGPLGCCR

The JNK3 inhibitor as described herein is an agent that reduces the level or activity of JNK3 in a target cell (e.g., a cardiomyocyte). JNK3 is a protein kinase of the MAPK family that is potently activated by a variety of environmental stress and pro-inflammatory cytokines. An inhibitor of JNK3 may be a nucleic acid, a polypeptide, or a small molecule that suppresses the expression the JNK3 gene or inhibits the bioactivity of the JNK3 protein. For example, an inhibitor can be an antisense oligonucleotide or an interfering RNA that targets one or more specific sites of the target gene or its mRNA so as to block gene transcription or protein translation. In some embodiments, the JNK3 inhibitor is a small hairpin RNA (shRNA) that silences the JNK3 gene via RNA interference. Such a shRNA may consist of 18-30 nucleotides (e.g., 20-25 nucleotides).

RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA disclosed herein can be a siRNA (containing two separate and complementary RNA chains) or a short hairpin RNA (i.e., a RNA chain forming a tight hairpin structure), both of which can be designed based on the sequence of the target gene. In one example, the shRNA that targets JNK3 (e.g., mouse JNK3) comprises the nucleotide sequence of CAATAGAGAGATCCAACATAA (SEQ ID NO:1).

An interfering RNA may be designed to target one or more isoforms of JNK3, for example in a human, monkey, mouse, or rat cell. In some embodiments, an interfering RNA is designed to target one or more isoforms of a human JNK3 mRNA. It should be appreciated that a skilled artisan would understand how to make and use an interfering RNA targeting a JNK3 mRNA from any organism, including any naturally-occurring isoforms thereof. In some embodiments, an interfering RNA is designed to target a human JNK3 mRNA. It should be appreciated that interfering RNAs may be designed to target one or more isoforms of JNK3 based on differences in the nucleotide sequence of the specific JNK3 isoforms. Methods for making and using interfering RNAs would be apparent to the skilled artisan and are within the scope of this disclosure. Exemplary methods for making and using interfering RNAs include, but are not limited to those described in Moore, C. B., et al., "Short Hairpin RNA (shRNA): Design, Delivery, and Assessment of Gene Knockdown," *Methods Mol Biol.*, 2010; 629: 141-158 and Naito, Y., et al., "siRNA Design Software for a Target Gene-Specific RNA Interference," *Front Genet.*, 2012 Jun. 11; 3:102; the contents of each of which are incorporated herein by reference for their disclosure relating to making and using interfering RNAs.

As an example, JNK3 mRNA, isoform 1 is provided in GenBank under gi|969536246|ref|NM_138982.3, which is incorporated by reference herein.

Optionally, an oligonucleotide inhibitor of JNK3 as described herein (e.g., an antisense nucleic acid, a small interfering RNA, or a microRNA) can contain non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability. In some examples, an oligonucleotide inhibitor of JNK3 as described herein may contain one or more locked nucleic acid residues (LNAs).

In one example, the oligonucleotide has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792,608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the oligonucleotide inhibitor of JNK3 described herein may include one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted C1 to C10 alkyl or C2 to C10 alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the oligonucleotide inhibitor of JNK3 as described herein may include one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

In some embodiments, the JNK3 inhibitor may be a JNK3 neutralizing antibody, which can be a full-length antibody or an antigen-binding fragment thereof. As used herein, the term "antibody" as includes but is not limited to polyclonal, monoclonal, humanized, chimeric, Fab fragments, Fv fragments, F(ab') fragments and F(ab')2 fragments, as well as single chain antibodies (scFv), fusion proteins and other synthetic proteins which comprise the antigen-binding site of the antibody.

Antibodies can be made by the skilled person using methods and commercially available services and kits known in the art. Methods of preparation of monoclonal antibodies are well known in the art and include hybridoma technology and phage display technology. Further antibodies suitable for use in the present disclosure are described, for example, in the following publications: Antibodies A Laboratory Manual, Second edition. Edward A. Greenfield. Cold Spring Harbor Laboratory Press (Sep. 30, 2013); Making and Using Antibodies: A Practical Handbook, Second Edition. Eds. Gary C. Howard and Matthew R. Kaser. CRC Press (Jul. 29, 2013); Antibody Engineering: Methods and Protocols, Second Edition (Methods in Molecular Biology). Patrick Chames. Humana Press (Aug. 21, 2012); Monoclonal Antibodies: Methods and Protocols (Methods in Molecular Biology). Eds. Vincent Ossipow and Nicolas Fischer. Humana Press (Feb. 12, 2014); and Human Monoclonal Antibodies: Methods and Protocols (Methods in Molecular Biology). Michael Steinitz. Humana Press (Sep. 30, 2013)).

Antibodies may be produced by standard techniques, for example by immunization with the appropriate polypeptide or portion(s) thereof, or by using a phage display library. If polyclonal antibodies are desired, a selected mammal (e.g., mouse, rabbit, goat, horse, etc) is immunized with an immunogenic polypeptide bearing a desired epitope(s), optionally haptenized to another polypeptide. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Serum from the immunized animal is collected and treated according to known procedures. If serum containing polyclonal antibodies to the desired epitope contains antibodies to other antigens, the polyclonal antibodies can be purified by immunoaffinity chromatography or any other method known in the art. Techniques for producing and processing polyclonal antisera are well known in the art.

An antibody specifically binds to JNKs if the antibody binds JNKs with a greater affinity than for an irrelevant polypeptide. In some embodiments, the antibody binds JNK3 with at least 5, or at least 10 or at least 50 times greater affinity than for the irrelevant polypeptide. In some embodiments, the antibody binds JNK3 with at least 100, or at least 1,000, or at least 10,000 times greater affinity than for the irrelevant polypeptide. Such binding may be determined by methods well known in the art, such surface plasmon resonance such as a Biacore® system. In some embodiments, the antibody has an affinity (as measured by a dissociation constant, $K_D$) for KIT of at least $10^{-7}$ M, $10^{-8}$ M, $10^{-9}$ M, $10^{-10}$ M, or $10^{-11}$ M.

In some examples, the anti-JNK3 antibodies described herein are full human antibodies. Full human antibodies can be obtained by using commercially available animals (e.g., mice) that have been engineered to express specific human immunoglobulin proteins. Transgenic animals that are designed to produce a more desirable (e.g., fully human antibodies) or more robust immune response may also be used for generation of humanized or human antibodies. Examples of such technology are XenoMouse™ from Amgen, Inc. (Fremont, Calif.) and HuMAb-Mouse™ and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

In other examples, the anti-JNK3 antibodies are humanized antibodies. Humanized antibodies refer to antibodies derived from non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation. Methods for constructing humanized antibodies are also well known in the art. See, e.g., Queen et al., Proc. Natl. Acad. Sci. USA, 86:10029-10033 (1989).

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

The JNK inhibitors described herein may also include small molecule inhibitors, such as JNK3 inhibitor XII and SR-3576, and those known in the art. See, e.g., Kamenecka et al., J Biol Chem 284, 12853-12861 (2009). JNK3 activity is regulated by phosphorylation, and the main phosphorylation sites for JNK3 function were Thr221 and Tyr223. Thus, inhibitors that modulate phosphorylation at, e.g., Thr221 and/or Tyr223 are also within the scope of the present disclosure. Other examples include, but are not limited to, SR3576, SP600125 (Cellagen Technology, Abcam), IQ 3 (Tocris Bioscience), TCS JNK 5a (Abcam), AS601245 (Abcam), and IQ-1S (Abcam).

The combinations or gene cocktails as described herein for use in prompting cardiomyocyte proliferation can include at least two of the FoxM1 enhancer, the Id1 enhancer, and the JNK3 inhibitor also described herein. In some examples, the combination includes one FoxM1 enhancer (e.g., a FoxM1 polypeptide or an expression vector for producing such) and one Id1 enhancer (e.g., an Id1 polypeptide or an expression vector for producing such). In other examples, the combination includes one FoxM1 enhancer (e.g., a FoxM1 polypeptide or an expression vector for producing such) and one JNK3 inhibitor (e.g., an antisense or shRNA that targets JNK3). In yet other examples, the combination includes one Id1 enhancer (e.g., an Id1 polypeptide or an expression vector for producing such) and one JNK3 inhibitor (e.g., an antisense or shRNA that targets JNK3). In a particular example, the combination includes one FoxM1 enhancer (e.g., a FoxM1 polypeptide or an expression vector for producing such), one Id1 enhancer (e.g., an Id1 polypeptide or an expression vector for producing such), and one JNK3 inhibitor (e.g., an antisense or shRNA that targets JNK3).

II. Promoting Cardiomyocyte Proliferation

Any of the combinations described herein can be used to promote cardiomyocyte proliferation, either in vitro or in vivo.

To practice the method described herein, one or more members of the combination can be mixed with a pharmaceutically acceptable carrier (excipient), including buffer, to form a pharmaceutical composition for use in promoting cardiomyocyte proliferation. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, each component of a combination is formulated in individual pharmaceutical compositions. In another example, more than one components of a combination are formulated in one pharmaceutical composition.

The pharmaceutical compositions to be used in the present methods can comprise pharmaceutically acceptable carriers, excipients, or stabilizers in the form of lyophilized formulations or aqueous solutions. Remington: The Science and Practice of Pharmacy 20th Ed. (2000) Lippincott Williams and Wilkins, Ed. K. E. Hoover. Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

In some examples, the pharmaceutical composition described herein comprises liposomes containing the FoxM1 enhancer, the Id1 enhancer, and/or the JNK3 inhibitor, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., the FoxM1 enhancer, the Id1 enhancer, and/or the JNK3 inhibitor) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing one or more of the enhancer/inhibitor described herein, which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span.™. 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can have a pH in the range of 5.5 to 8.0. The emulsion compositions can be those prepared by mixing a FoxM1 enhancer, an Id1 enhancer, and/or a JNK3 inhibitor with Intralipid™ or the components thereof (soybean oil, egg phospholipids, glycerol and water).

To promote cardiomyocyte cell proliferation in a subject in need of the treatment, an effective amount of one or more pharmaceutical compositions comprising any of the combinations described herein (e.g., including at least two of a FoxM1 enhancer, an Id1 enhancer, and a JNK3 inhibitor) can be administered to the subject (e.g., a human subject) via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the FoxM1 enhancer, the Id1 enhancer, and/or the JNK3 inhibitor can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a heart damage or degenerative disorder. In some examples, the human subject has, is suspected of having or at risk for myocardial infarction. A subject having heart damage or a heart degenerative disorder can be identified by routine medical examination, e.g., laboratory tests, heart functions tests, heart biopsy, CT scans, or ultrasounds. A subject suspected of having heart damage or heart degenerative disorder might show one or more symptoms of the disorder. A subject at risk for heart damage or heart degenerative disorder can be a subject having one or more of the risk factors for that disorder.

The subject to be treated by the methods described herein can be any age or stage of development. In some embodiments, the subject is an embryo, a fetus, a neonate, a child, an adolescent, or an adult. As used herein, a "neonate" refers to a newborn organism (e.g., a human or mouse) that is 30 days old or less. As used herein, an "adult" refers to an organism (e.g., a human or mouse) that has reached sexual maturity.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, polypeptides that are compatible with the human immune system, such as human FoxM1, human Id1, or functional fragments thereof, may be used to prolong half-life of the polypeptide and to prevent the polypeptide being attacked by the host's immune system. Frequency of administration may be determined and adjusted over the course of therapy, and is generally, but not necessarily, based on treatment and/or suppression and/or amelioration and/or delay of the heart disease. Alternatively, sustained continuous release formulations of a FoxM1 enhancer, an Id1 enhancer, and/or a JNK3 inhibitor may be appropriate. Various formulations and devices for achieving sustained release are known in the art.

In one example, dosages for a FoxM1 enhance, an Id1 enhancer, and a JNK3 inhibitor, as described herein, may be determined empirically in individuals who have been given one or more administration(s) of the combination of FoxM1 enhancer, the Id1 enhancer, and/or the JNK3 inhibitor. Individuals are given incremental dosages of the active agents. To assess efficacy of the active agents, an indicator of the heart damage can be followed.

Generally, for administration of any of the FoxM1 enhancer, the Id1 enhancer, and/or the JNK3 inhibitor described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate the heart disorder, or a symptom thereof. An exemplary dosing regimen comprises administering an initial dose of about 2 mg/kg, followed by a weekly maintenance dose of about 1 mg/kg of the enhancer and/or inhibitor, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the active agent used) can vary over time.

When the active agent is a small molecule, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a FaxM1 enhancer, a Id1 enhancer, and a JNK3 inhibitor will depend on the specific agent (or compositions thereof) employed, the type and severity of the heart disorder, whether the active agent is administered for preventive or therapeutic purposes, previous therapy, the patient's clinical history and response to the antagonist, and the discretion of the attending physician. Typically the clinician will administer a FoxM1 enhancer (e.g., a FoxM1 polypeptide), an Id1 enhancer (e.g., an Id1 polypeptide), and/or a JNK3 inhibitor (e.g., a shRNA specific to JNK3), until a dosage is reached that achieves the desired result. Administration of the active agents can be continuous or intermittent, depending, for example, upon the recipient's physiological condition, whether the purpose of the administration is therapeutic or prophylactic, and other factors known to skilled practitioners. The administration of the active agents may be essentially continuous over a preselected period of time or may be in a series of spaced dose, e.g., either before, during, or after developing the heart disorder.

As used herein, the term "treating" refers to the application or administration of a composition including the combination (or gene cocktail) described herein, comprising at least two of a FoxM1 enhancer, an Id1 enhancer, and a JNK3 inhibitor, to a subject, who has heart damage or a heart degenerative disorder, a symptom of the damage/disorder, or a predisposition toward the disease, with the purpose to cure, heal, alleviate, relieve, alter, remedy, ameliorate, improve, or affect the disorder, the symptom of the disease, or the predisposition toward the disease.

Alleviating heart damage or the heart degenerative disorder includes delaying the development or progression of the disease, or reducing disease severity. Alleviating the disease does not necessarily require curative results. As used therein, "delaying" the development of a disease (such as a heart degenerative disorder) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of heart damage or heart degenerative disorder includes initial onset and/or recurrence.

In some embodiments, the active agent (e.g., a FoxM1 enhancer, an Id1 enhancer, and a JNK3 inhibitor) described herein is administered to a subject in need of the treatment at an amount sufficient to enhance or reduce the level of the target gene product (FoxM1, Id1, and JNK3) by at least 20% (e.g., 30%, 40%, 50%, 60%, 70%, 80%, 90% or greater).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the active agent(s) and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the enhancer/inhibitor, can be dissolved and administered in a pharmaceutical excipient such as Water-for-Injection, 0.9% saline, or 5% glucose solution.

In one embodiment, one or more of the FoxM1 enhancer, the Id1 enhancer, and the JNK3 inhibitor are administered via site-specific or targeted local delivery techniques. Examples of site-specific or targeted local delivery techniques include various implantable depot sources of the active agents or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense oligonucleotide or an expression vector can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides of the FoxM1 enhancer, the Id1 enhancer, and/or the JNK3 inhibitor described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), adenoal virus vectors, and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed. In some examples, one or more of the FoxM1 enhancer, Id1 enhancer, or JNK3 inhibitor are delivered via an AAV viral vector.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based FoxM1 enhancer, Id1 enhancer, and/or JNK3 inhibitor.

In some embodiments, any of the combinations of a FoxM1 enhancer, an Id1 enhancer, and a JNK3 inhibitor as described herein can be used in vitro to promote cardiomyocyte proliferation. Cardiomyocyte cells, derived from a suitable donor or differentiated from pluripotent or embryonic stem cells, can be cultured in the presence of the combination of a FoxM1 enhancer, an Id1 enhancer, and a JNK3 inhibitor under suitable conditions allowing for the proliferation of the cardiomyocyte cells induced by the enhancer/inhibitor combination. The proliferated cardiomyocyte cells can be administered to a subject in need of the treatment, e.g., a human subject having, suspected of having, or at risk for heart damage, for treating the heart disorder. In some examples, the cardiomyocyte cells are autologous, i.e., derived from the same human subject. In other examples, the cardiomyocyte cells are allogenic, e.g., derived from a different human subject.

III. Kits for Use in Promoting Cardiomyocyte Proliferation

The present disclosure also provides kits for use in promoting cardiomyocyte proliferation. Such kits can include one or more containers comprising at least two of a FoxM1 enhancer, an Id1 enhancer, and a JNK3 inhibitor. In some embodiments, the FoxM1 enhancer is a FoxM1 polypeptide or an expression vector for producing such. In some embodiments, the Id1 enhancer is an Id1 polypeptide or an expression vector for producing such. In some embodiments, the JNK3 inhibitor is a small interfering RNA targeting JNK3. In some embodiments, the kit comprises a FoxM1 enhancer, an Id1 enhancer, and a JNK3 inhibitor.

In some embodiments, the kit can comprise instructions for use in accordance with any of the methods described herein. The included instructions can comprise a description of administration of the FoxM1 enhancer, the Id1 enhancer, and/or the JNK3 inhibitor to treat, delay the onset, or alleviate heart damage or a heart degenerative disorder according to any of the methods described herein. The kit may further comprise a description of selecting an individual suitable for treatment based on identifying whether that individual has heart damage or the heart degenerative disorder. In still other embodiments, the instructions comprise a description of administering one or more of the active agents to an individual at risk of heart damage/disorder.

The instructions relating to the use of a FoxM1 enhancer, an Id1 enhancer, and the JNK3 inhibitor generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the heart disorder. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR:

The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: A Therapeutic Gene Cocktail for Heart Regeneration

Materials and Methods
(i) Isolation of Cardiomyocytes and Non-Cardiomyocytes from Neonatal Heart Cardiomyocytes and non-cardiomyocytes were isolated from 2- or 3-day-old C57BL/6 mice and the procedure was modified from the protocol described previously (Condorelli, Morisco et al. FASEB J. 16(13):1732-1737; 2002). In brief, the heart tissue was minced and digested by 1 mg/ml Trypsin (Sigma-Aldrich) at 4° C. for 2 hours after removal of atrium and aorta. The minced tissues were treated with 0.8 mg/ml Collagenase II (Invitrogen) at 37° C. for 15 minutes, and the cells were collected after filtering with 40 um strainer for clearance of debris.

Pure cardiomyocytes were purified by staining with mitochondrial dye, tetramethylrhodamine methyl ester perchlorate (TMRM) (Life Technology), as population with the highest intensity analyzed and sorted by fluorescence activated cell sorter FACS (Hattori, et al., Nat Methods 7(1): 61-66; 2010). Lower TMRM staining population was also collected as the non-cardiomyocytes for comparison.

(ii) Reprogramming Procedure

The reprogramming experiment was modified from the standard procedure that mentioned before (Takahashi et al., Cell 126(4):663-676; 2006). In brief for the modified part, the time point for re-seeding on the feeder cells was prolonged to day 10 instead of day 3. The iPS medium was modified with GMEM basal medium with 15% FBS instead of DMEM with 10% KOSR or FBS.

For secondary reprogramming system with doxycycline regulated OSKM transgenic mice, the concentration of doxycycline was administrated as 1 ug/ml every day during early reprogramming.

(iii) In Vitro Differentiation of iPS Cells

The induced pluripotent stem cells (iPS cells) were cultured without feeder cells for 2 days and then were collected to resuspend in differentiation medium with GMEM basal medium (Invitrogen) with 10% FBS. The suspended cells were diluted and spotted on the dish lids as 600 cells for each drop. After hanging-drop culture for 3 days, the embryoid bodies were seeded on gelatin-coated dish for another 7 days. These differentiated cells were fixed with 4% paraformaldehyde and processed the immunofluorescence procedure.

(iv) Teratoma Formation

About $1\times10^6$ iPS cells were subcutaneously injected into 6- to 8-week-old NOD-scid mice, and the teratoma could be observed after 3-4 weeks. The tumors were fixed and embedded in paraffin and then the sections were stained with Hematoxylin & Eosin (Sigma-Aldrich).

(v) Transcriptomic Analysis

Samples from different reprogramming time points were hybridized to a Mouse Oligo Microarray (Agilent) following the manufacturer's procedure, and arrays were scanned with Microarray Scanner System (Agilent). All Data were analyzed by GeneSpring GX software (Agilent), and Gene Ontology analysis was done by DAVID software (Huang da, et al., Nat Protoc 4(1):44-57; 2009).

(vi) Production and Purification of Recombinant Adenoviral Vectors

Foxm1, Id1, and Hmgb2 cDNA were amplified from total reverse-trancriptized cDNA purified from C57BL/6 mice with Phusion High-Fidelity PCR Master Mix (New England Biolabs). The amplified fragment was cloned into the site next to ires-EGFP of pENTR plasmid. These specific gene carrying pENTR plasmids were then recombined into pAd/PL-DEST plasmids following pAd/PL-DEST Gateway Vector Kit instruction (Invitrogen).

These specific gene carrying pAd/PL-DEST were performed to produce adenovirus with specific gene and EGFP expression following the procedure as previously described (Luo et al., NT Protoc 2(5):1236-1247). The viral condensation was completed by $CsCl_2$ gradient centrifugation.

(vii) Treatment of JNK3 Inhibitor XII, SR-3576

JNK3 inhibitor XII, SR-3576 (Millipore) was designed specifically for JNK3 and it was administrated as 1 uM in neonatal CMs in vitro for 3 hours.

(viii) Injection of Adenoviral Vectors in Neonatal and Adult Mice

For neonatal mice, adenoviral infection of hearts was mentioned previously in detail (Christensen et al., Circulation 101(2):178-184; Ebelt et al., Cardiovasc Res. 80(2): 219-226; 2008) and One-day-old mice were anaesthetized by cooling on ice for 2 minutes and were injected into the thoracic cavity at the left parasternal position with Hamiliton syringe with 30-gauge needle and then put back to their mother feeding for 12 days. The mice were then sacrificed and hearts were collected for following experiments.

For adult mice, intracardiac injection was performed at the dose of $1\times10^{11}$ viral particles. For therapy, adenovirus was injected to the border zone of the injured heart at 3 sites right after myocardial infarction.

(ix) Myocardial Infarction

Mice (8- to 10-week-old) were anesthetized with an inhalation anesthetics of isofluorane, endotracheally intubated and placed on a rodent ventilator. The permanent left anterior descending (LAD) coronary artery ligation was visualized and occluded with a prolene suture after removing the pericardium. The whitening of a region of the left ventricle was confirmed immediately post-ligation as successful myocardial infarction.

(x) Echocardiography

Transthoracic two-dimensional echocardiography was analyzed using a Vivid-q Ultrasound (General Electric Company) equipped with a 5.0-13.0 MHz intraoperative probe. M-mode tracings in parasternal short axis view were used to measure left ventricular anterior and posterior wall thickness and internal diameter at end-systole and end-diastole for calculating left ventricular fractional shortening and ejection fraction.

(xi) Masson's Trichrome Staining

Heart tissues were collected and fixed in 4% paraformaldehyde, and embedded in paraffin. The sections were performed following standard protocols, and decided the infarct size by measuring the percentage of fibrosis of the total left ventricular area.

(xii) Immunofluorescence

The cells were fixed with 4% paraformaldehyde and permeabilized by 0.3% triton X-100 in blocking buffer with 5% goat serum in PBS for 1 hour. Then, the cells were stained with primary antibodies, OCT-4 (Santa Cruz), SOX-2 (Millipore), KLF-4 (Abcam), Nanog (Reprocell) for pluripotency confirmation of iPS cells; Nestin (R & D), α-Smooth muscle actin (Sigma), and α-Fetoprotein (R & D) for in vitro differentiation of iPS cells; and Ki-67 (Genetex), histone H3 phosphorylated at serine 10 (Millipore), Aurora B kinase (Abcam) for gene screening. As for SSEA-1 (Biolegend) staining, the procedure should skip the permeabilization step. The respective secondary antibodies conjugated with Alexa fluor-488 or -568 (Life Technology) were performed for 1 hour after washing with PBS for 3 times, and the nucleus were stained with DAPI (Life Technology) for 5 minutes.

The tissue sections were deparaffinized, rehydrated, and done antigen-retrieval with boiling sodium citrate for 5 minutes twice. Then, the sections were followed the same immunofluorescence procedure as mentioned previously, and Wheat germ agglutinin (WGA) conjugated with Alexa fluor-488 (Life Technology) were performed to stain the membrane of the tissues.

For gene screening, the cells were processed the immunofluorescence procedure with Ki67 and DAPI staining and image acquisition was performed by ImageXpress Micro High content screening microscope (Molecular Devices).

For reprogramming efficiency, AP substrate kit, Vector Red substrate kit (Vector Laboratories, Burlingame, Calif.) was used for determination of iPSC-like colony numbers. The reprogramming efficiency was calculated by AP$^+$ colony numbers/lentiviral infected cell numbers.

(xiii) Quantitative Real-Time PCR

Reverse transcription were completed following the protocol of SuperScript III Reverse-Transcriptase kit (Life Technology). SYBR Green Real-Time PCR master mixes were used to quantify each gene expression, and GAPDH were performed for normalization.

(xiv) Statistics

All statistical data was analyzed by Prism Gaphpad and shown as mean±standard error of the mean (S.E.M.). Unpaired, two-tailed Student's t-test and one-way ANOVA were applied for statistical comparison and the value of $P<0.05$ was considered a significant difference.

Results

Figure 1B:
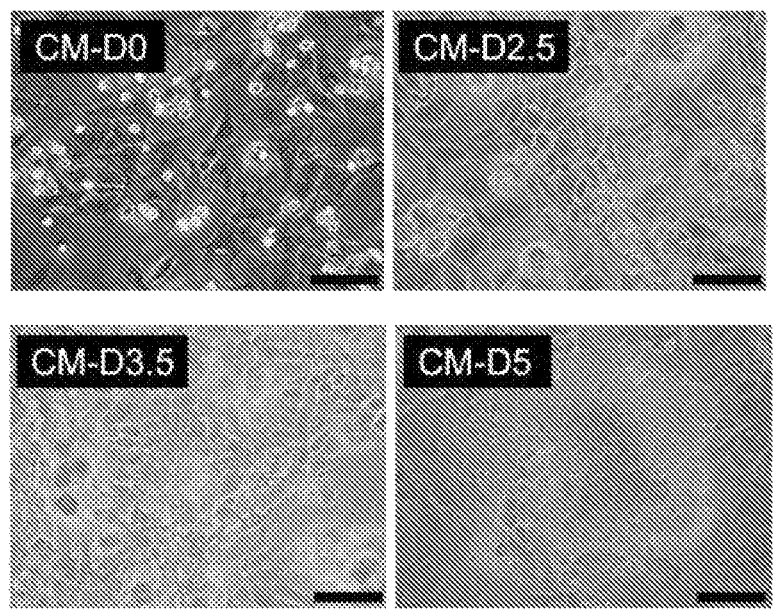
Figure 1C:
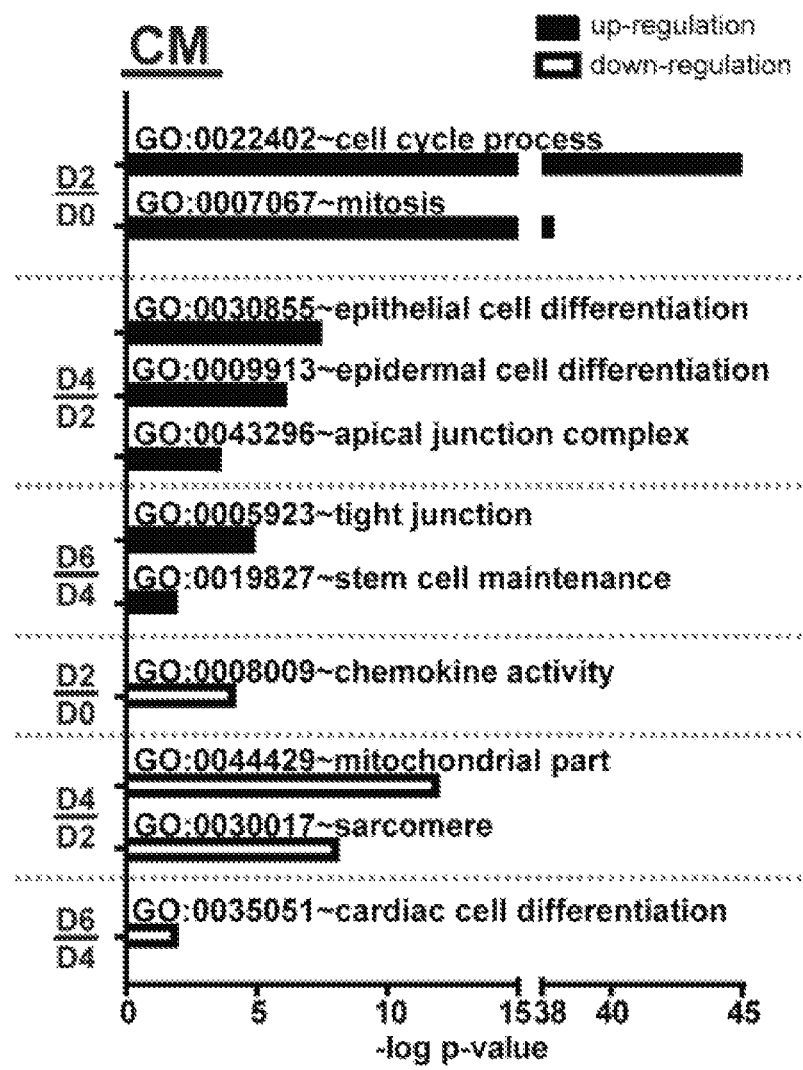

Different time points during cardiomyocytes (CM) reprogramming were investigated by administrating transgenic mice with doxycycline inducible four Yamanaka's 4 factors based on the different morphologies and microarray analysis. FIG. 1A. The results showed that the enhanced CM proliferation was observed at reprogramming day 2. FIG. 1B and FIG. 1C.

Figure 2A:
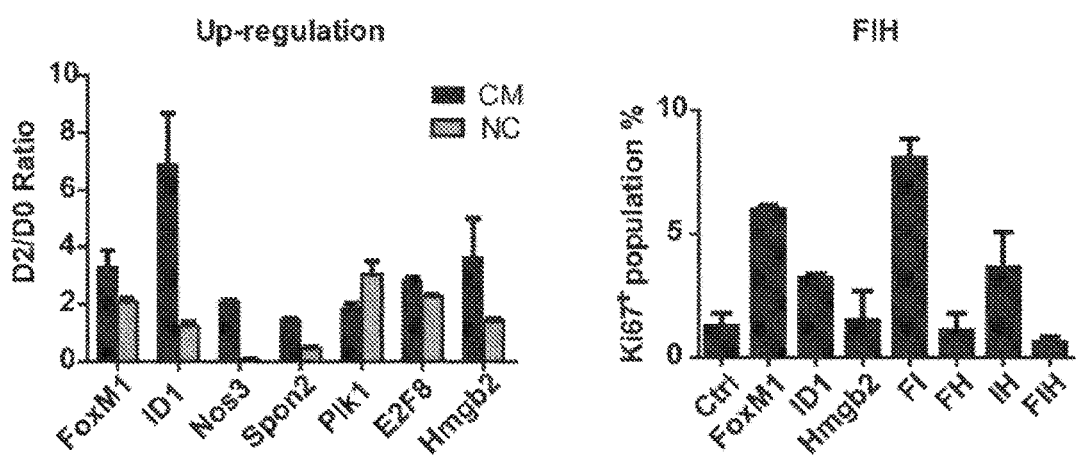
FIGS. 2A-2C are charts showing selection of genes that play roles in CM proliferation.
Figure 2B:
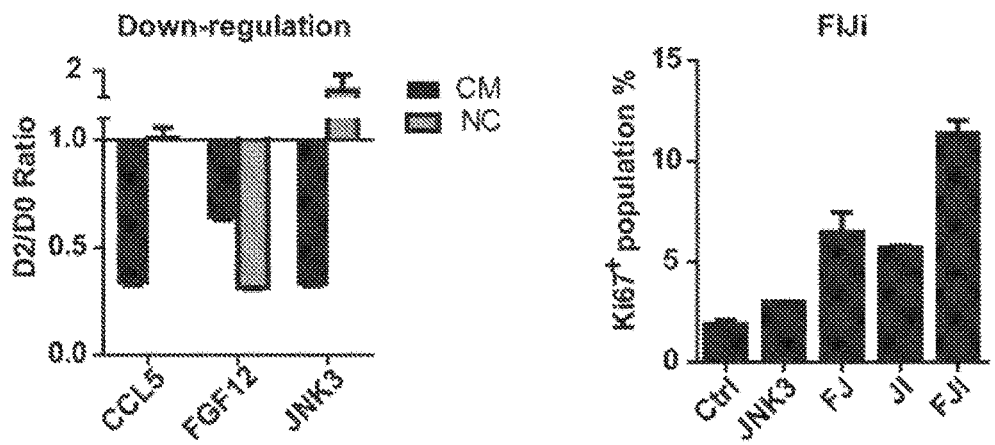
Figure 2C:
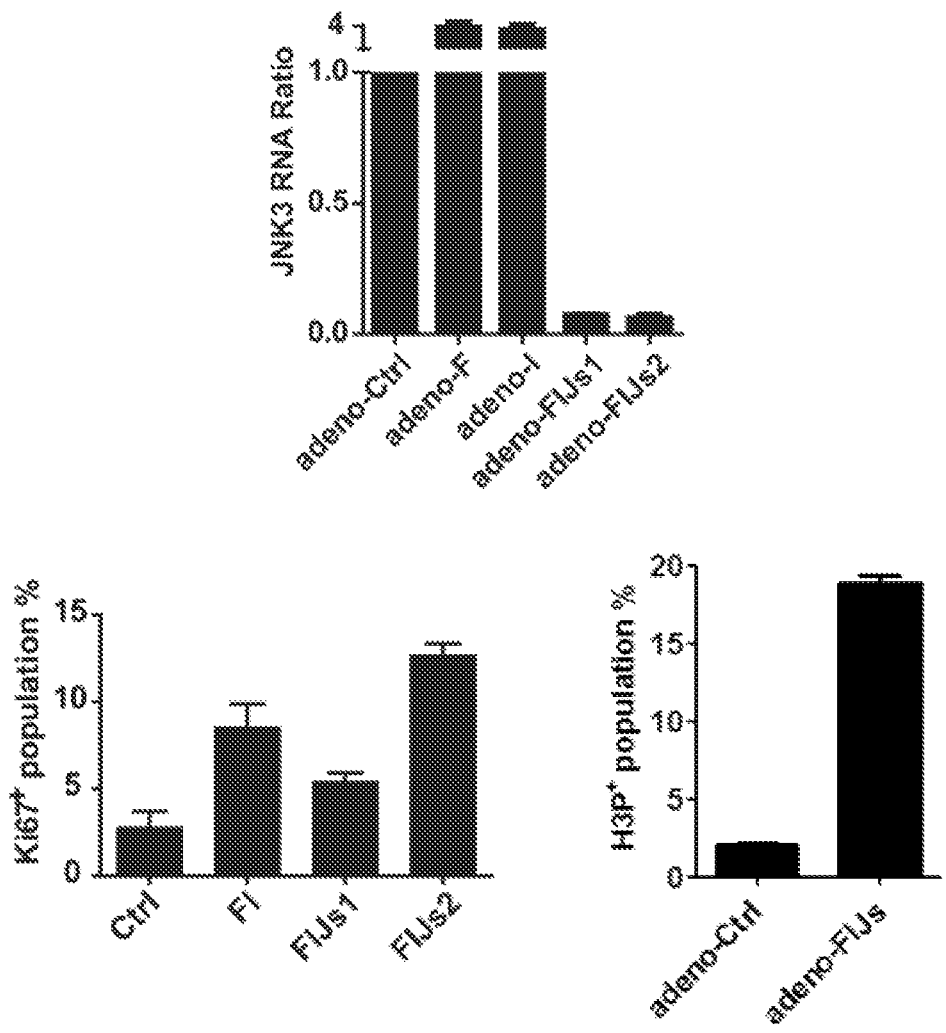

Genes selected from microarray analysis as described herein were tested for their role in neonatal CM proliferation by measuring the percentage of the Ki-67 positive population. Antigen Ki-67 is a nuclear protein that is associated with cellular proliferation. Specific over-expression or knockdown of gene expression in CM was achieved by injection of adenoviral vectors carrying the desired gene(s) or by treatment with suitable inhibitors. Double or triple combinations of FoxM1, Id1, and Jnk3 inhibitor were used to treat neonatal CMs in vitro and the results showed that the treatments led to 7 times higher percentage of the Ki67 or H3P positive population than control group, indicating that the treatments of the double or triple combination significantly enhanced CM proliferation. FIGS. 2A-2C.

Figure 3A:
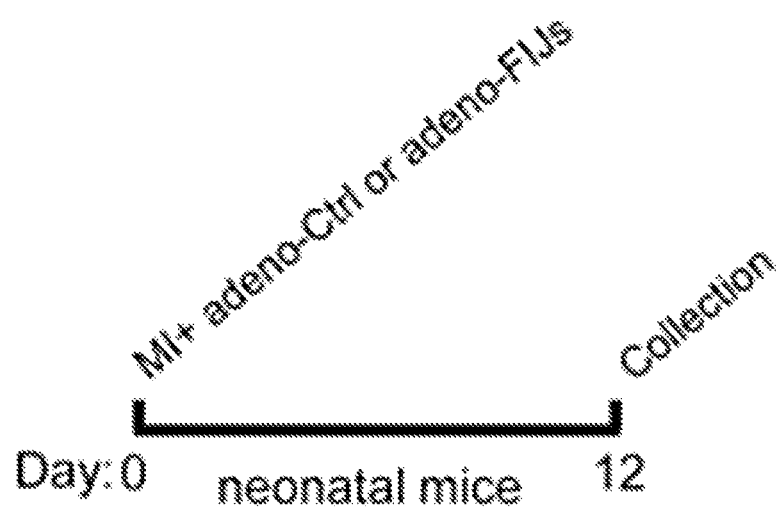
FIGS. 3A-3C are diagrams showing the triple combined treatment described herein for heart development in vivo.
Figure 3B:
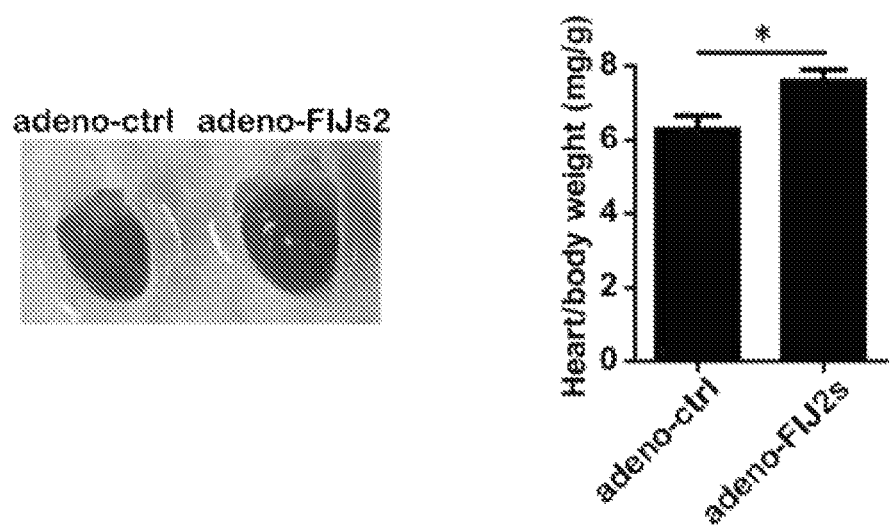
Figure 3C:
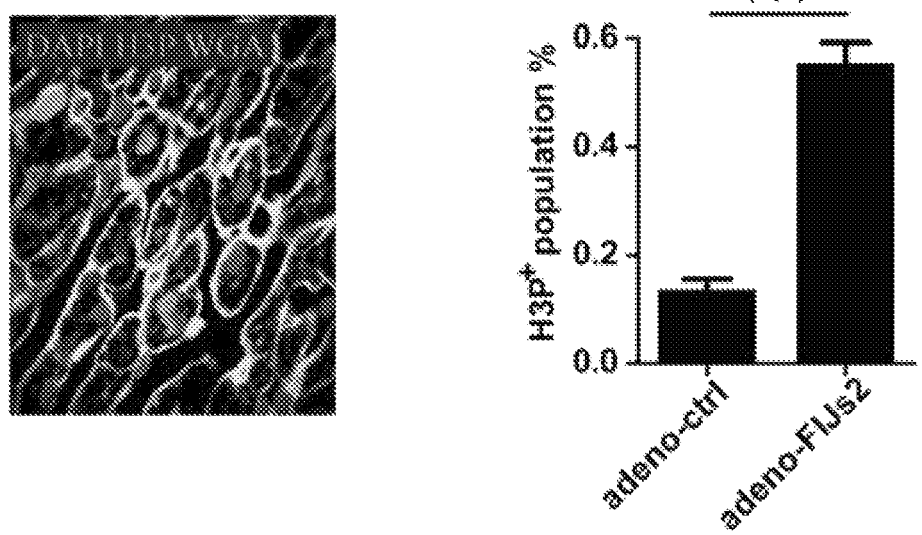
Figure 4A:
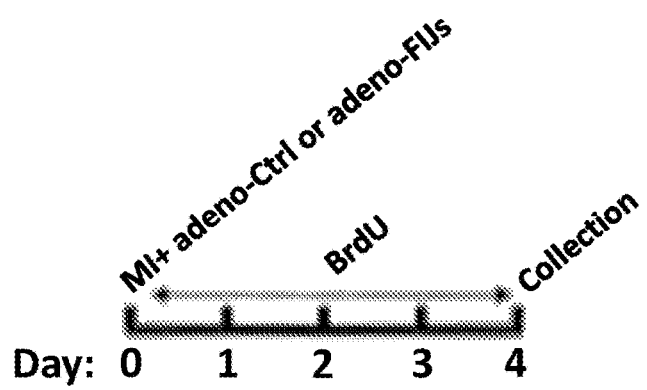
FIGS. 4A-4E are diagrams showing the triple combined treatment described herein for heart regeneration after injury in vivo.
Figure 4B:
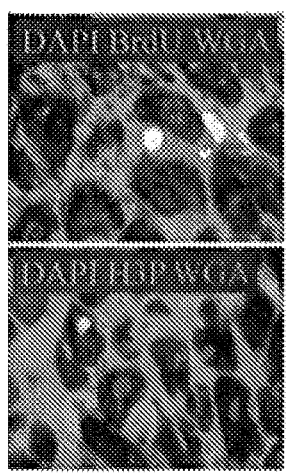
Figure 4B:
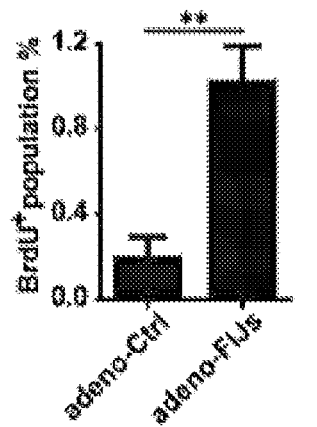
Figure 4B:
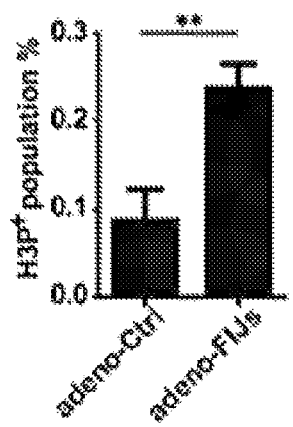
Figure 4C:
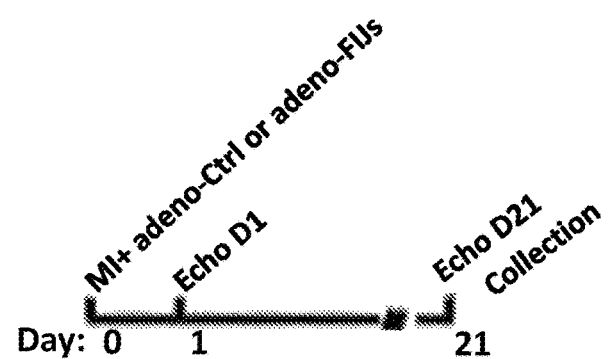
Figure 4D:
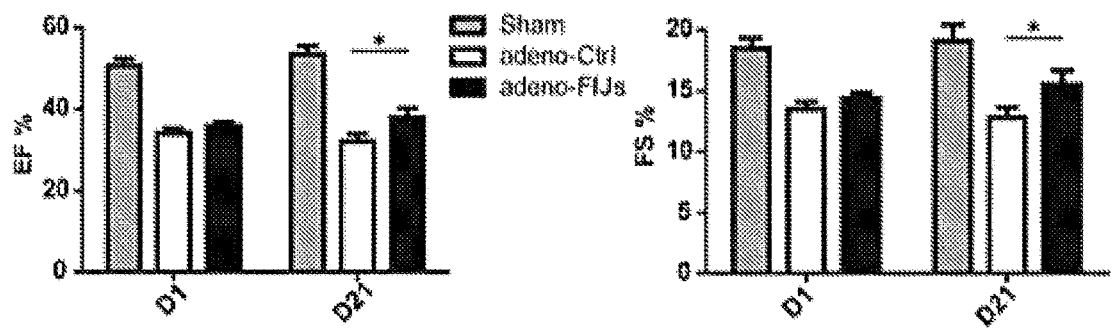
Figure 4E:
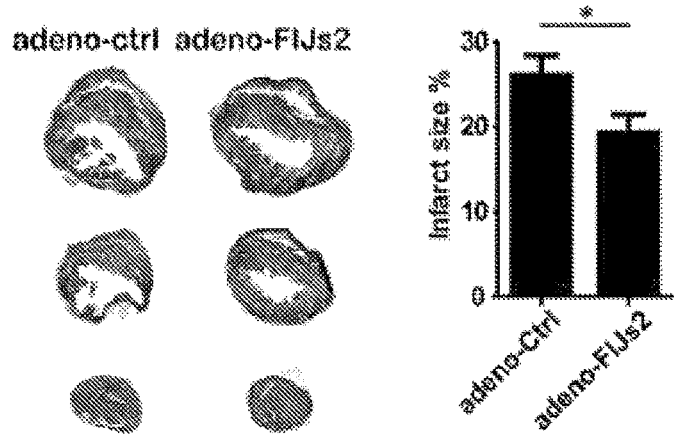

The triple combination of FoxM1, Id1, and Jnk3-shRNA was administrated to one-day-old neonatal mice in vivo. The treated mice showed higher value of heart-to-body weight and higher percentage of the H3P positive population as compared to control mice. FIG. 3A and FIG. 3B. These results confirmed that triple combined gene cocktail was effective in promoting CM proliferation during heart development.

The triple gene cocktail described herein was administrated to adult mice at a border zone of the heart after myocardial infarction. Heart function was improved in the treated mice due to the enhanced proliferative ability of CMs induced by the gene cocktail. Measuring by echocardiography and fibrosis assays.

Example 2: A Defined Gene Cocktail Significantly Increases Adult Cardiomyocyte Proliferation In Vivo Materials and Methods (i) Adult Cardiomyocyte Isolation Adult ventricular CMs were isolated from male mice on a Langendorff apparatus. The hearts were removed from the anaesthetized mice after heparinization for 10 mins, and then were cannulated for retrograde perfusion with $Ca^{2+}$-free Tyrode solution (NaCl 120.4 mmol/L, KCl 14.7 mmol/L, $KH_2PO_4$ 0.6 mmol/L, $Na_2HPO_4$ 0.6 mmol/L, $MgSO_4$ 1.2 mmol/L, HEPES 1.2 mmol/L, $NaHCO_3$ 4.6 mmol/L, Taurine 30 mmol/L, BDM 10 mmol/L, Glucose 5.5 mmol/L).

After 3-minutes of perfusion, the solution mixed with $Ca^{2+}$-free Tyrode solution supplemented with collagenase B (0.4 mg/g body weight, Roche), collagenase D (0.3 mg/g body weight, Roche) and protease type XIV (0.05 mg/g body weight, Sigma-Aldrich) were used to digest the hearts. After digestion, the ventricles were cut from the cannula and teased into small pieces in the digestion solution neutralized by the $Ca^{2+}$-free Tyrode solution containing 10% FBS. Adult CMs were dissociated from the digested tissues by gentle pipetting and collected after removing the un-digested tissues by filtering through a nylon mesh of 250 μm pore size.

Results

Figure 5A:
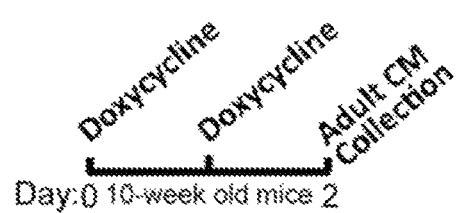
FIGS. 5A-5E are diagrams showing gene screening for adult CM proliferation in vivo by mimicking early reprogramming.
Figure 5B:
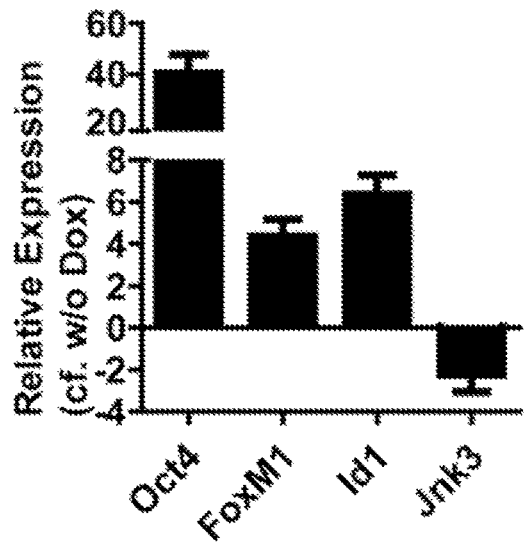
Figure 5C:
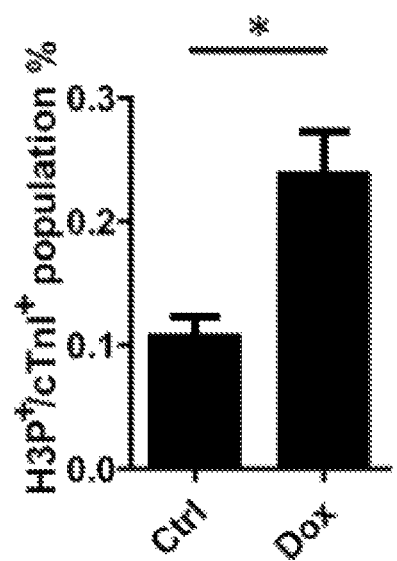

Changes in the expression of Oct4, FoxM1, Id1, and Jnk3 were confirmed in vivo by injecting doxycycline into OSKM transgenic mice and isolating adult CMs after two days (FIG. 5A). Overexpression of Oct4 was confirmed for the successful treatment of doxycycline injection in vivo (FIG. 5B). As expected, FoxM1 and Id1 showed higher expression and Jnk3 was significantly down-regulated compared to control CMs (FIG. 5B). In addition, significantly higher H3P$^+$ population of adult CMs (2×) was found two days after doxycycline treatment (FIG. 5C).

Figure 5D:
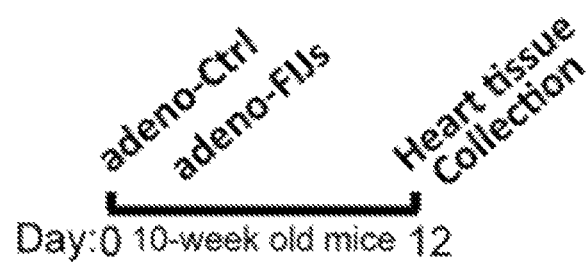
Figure 5E:
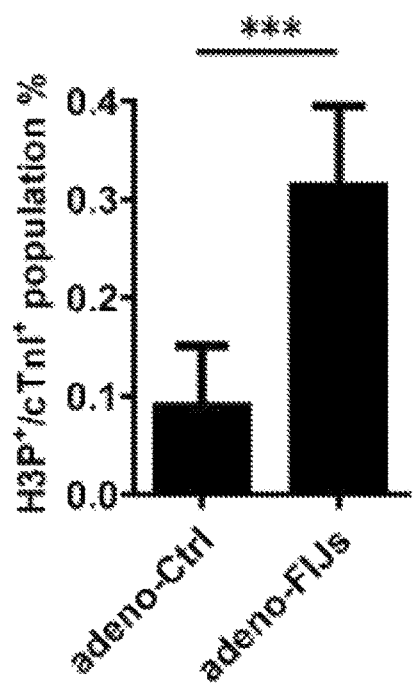

Furthermore, the ability of FIJs treatment to enhance adult CM proliferation in vivo was demonstrated by direct injection into the heart of 10-week old mice (FIG. 5D). After twelve days, the H3P$^+$ population was 3.5 times higher in FIJs-treated mice than control-treated mice (FIG. 5E). The combination of these results shows that FIJs treatment could efficiently enhance adult CM proliferation in vivo.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for promoting heart regeneration, comprising administering to a subject in need thereof an effective amount of a combination comprising at least two of the following:
   (i) a FoxM1 enhancer, which is a FoxM1 polypeptide or an agent selected from the group consisting of 5' AMP-activated protein kinase (AMPK), osteopontin, CXCL12, and TNF-α;
   (ii) an Id1 enhancer, which is a Id1 polypeptide or an agent selected from the group consisting of a bone morphogenetic protein (BMP), leukemia inhibitory factor (LIF), glucose, insulin, 5-aza-2'-deoxycytidine (DAC), and HDAC inhibitor trichostatin A (TSA); and
   (iii) a JNK3 inhibitor, which is an antisense oligonucleotide or an interfering RNA that targets a JNK3 gene, or a small molecule inhibitor selected from the group consisting of JNK3 inhibitor XII, SR-3576, SR3576, SP600125, IQ3, TCS JNK 5a, AS601245, and IQ-1S.

2. The method of claim 1, wherein the subject is administered an expression vector for producing the FoxM1 polypeptide.

3. The method of claim 1, wherein the subject is administered an expression vector for producing the Id1 polypeptide.

4. The method of claim 1, wherein the combination contains all of (i)-(iii).

5. The method of claim 1, wherein the administering step is performed by delivering to the subject one or more expression vectors for producing the FoxM1 polypeptide, the Id1 polypeptide, and a shRNA that targets the JNK3 gene.

6. The method of claim 5, wherein the one or more expression vectors are viral vectors or non-viral vectors.

7. The method of claim 6, wherein the viral vectors are adenoviral vectors or adeno-associated viral vectors.

8. The method of claim 1, wherein the subject is a human patient having, suspected of having, or at risk for myocardial infarction.

9. The method of claim 8, wherein the combination is administered to a site having or suspected of having a heart degenerative disorder.

10. The method of claim 1, wherein the subject is a neonate.

11. The method of claim 1, wherein the subject is an adult.

12. The method of claim 1, wherein the FoxM1 polypeptide comprises the amino acid sequence of:
   (i) residues 232-694 of SEQ ID NO: 2;
   (ii) residues 232-641 of SEQ ID NO: 3; or
   (iii) residues 232-656 of SEQ ID NO: 4.

13. The method of claim 12, wherein the FoxM1 polypeptide comprises the amino acid sequence of any one of SEQ ID NOs: 2-4.

14. The method of claim 1, wherein the Id1 polypeptide comprises the amino acid sequence of any one of SEQ ID NOs: 5-6.

15. The method of claim 1, wherein the interfering RNA that targets the JNK3 gene comprises the nucleotide sequence of SEQ ID NO: 1.

16. A method for promoting cardiomyocyte proliferation and differentiation, the method comprising culturing cardiomyocyte cells in the presence of at least two of the following:
   (i) a FoxM1 enhancer, which is a FoxM1 polypeptide or an agent selected from the group consisting of 5' AMP-activated protein kinase (AMPK), osteopontin, CXCL12, and TNF-α;
   (ii) an Id1 enhancer, which is a Id1 polypeptide or an agent selected from the group consisting of a bone morphogenetic protein (BMP), leukemia inhibitory factor (LIF), glucose, insulin, 5-aza-2'-deoxycytidine (DAC), and HDAC inhibitor trichostatin A (TSA); and
   (iii) a JNK3 inhibitor, which is an antisense oligonucleotide or an interfering RNA that targets a JNK3 gene, or a small molecule inhibitor selected from the group consisting of JNK3 inhibitor XII, SR-3576, SR3576, SP600125, 103, TCS JNK 5a, AS601245, and IQ-1S.

17. The method of claim 16, wherein the cardiomyocyte cells are cultured in the presence of all of (i) (iii).

18. The method of claim 16, wherein the cardiomyocyte cells are cultured in the presence of an expression vector for producing the FoxM1 polypeptide.

19. The method of claim 16, wherein the cardiomyocyte cells are cultured in the presence of an expression vector for producing the Id1 polypeptide.

20. The method of claim 16, wherein the cardiomyocyte cells are cultured in the presence of a shRNA that targets the JNK3 gene.

21. The method of claim 16, wherein the method further comprises delivering the cultured cardiomyocyte cells to a subject in need thereof.

22. The method of claim 21, wherein subject in need thereof is a human patient having, suspected of having, or being at risk for a heart degenerative disorder.

23. The method of claim 21, wherein the subject is a neonate.

24. The method of claim 21, wherein the subject is an adult.

25. The method of claim 21, wherein the cardiomyocyte cells are autologous.

26. The method of claim 21, wherein the cardiomyocyte cells are allogenic.

27. The method of claim 16, wherein the FoxM1 polypeptide comprises the amino acid sequence of:
   (i) residues 232-694 of SEQ ID NO: 2;
   (ii) residues 232-641 of SEQ ID NO: 3; or
   (iv) residues 232-656 of SEQ ID NO: 4.

28. The method of claim 27, wherein the FoxM1 polypeptide comprises the amino acid sequence of any one of SEQ ID NOs: 2-4.

29. The method of claim 16, wherein the Id1 polypeptide comprises the amino acid sequence of any one of SEQ ID NOs: 5-6.

30. The method of claim 16, wherein the interfering RNA that targets the JNK3 gene comprises the nucleotide sequence of SEQ ID NO: 1.

\* \* \* \* \*